US008883776B2

(12) United States Patent
Letavic et al.

(10) Patent No.: US 8,883,776 B2
(45) Date of Patent: *Nov. 11, 2014

(54) CYCLOALKYLOXY- AND HETEROCYCLOALKYLOXYPYRIDINE COMPOUNDS AS MODULATORS OF THE HISTAMINE $H_3$ RECEPTOR

(75) Inventors: Michael A. Letavic, San Diego, CA (US); Emily M. Stocking, Encinitas, CA (US)

(73) Assignee: Janssen Pharmaceutica N.V., Beerse (BE)

( * ) Notice: Subject to any disclaimer, the term of this patent is extended or adjusted under 35 U.S.C. 154(b) by 915 days.

This patent is subject to a terminal disclaimer.

(21) Appl. No.: 12/272,268

(22) Filed: Nov. 17, 2008

(65) Prior Publication Data

US 2009/0131415 A1 May 21, 2009

Related U.S. Application Data

(60) Provisional application No. 60/989,246, filed on Nov. 20, 2007.

(51) Int. Cl.
*C07D 401/14* (2006.01)
*A61K 31/34* (2006.01)
*A61K 31/443* (2006.01)
*A61K 31/496* (2006.01)
*A61K 31/5513* (2006.01)
*C07D 409/14* (2006.01)
*C07D 407/14* (2006.01)

(52) U.S. Cl.
CPC ............ *C07D 407/14* (2013.01); *C07D 409/14* (2013.01); *C07D 401/14* (2013.01)
USPC ....... 514/218; 514/253.12; 540/575; 544/360

(58) Field of Classification Search
None
See application file for complete search history.

(56) References Cited

U.S. PATENT DOCUMENTS

| 3,538,106 | A | 11/1970 | Hoffmann et al. |
| 4,792,547 | A | 12/1988 | Itoh et al. |
| 5,384,305 | A | 1/1995 | Foster et al. |
| 5,780,393 | A | 7/1998 | Newton |
| 6,201,007 | B1 | 3/2001 | Ito et al. |
| 6,339,045 | B1 | 1/2002 | Kanno et al. |
| 6,399,607 | B1 | 6/2002 | Welch et al. |
| 6,645,990 | B2 | 11/2003 | Askew et al. |
| 7,067,507 | B2 * | 6/2006 | Pulley et al. .................. 514/183 |
| 7,423,147 | B2 | 9/2008 | Carruthers et al. |
| 2003/0125339 | A1 | 7/2003 | Chen et al. |
| 2004/0014744 | A1 | 1/2004 | Haviv et al. |
| 2004/0019039 | A1 | 1/2004 | Dorwald et al. |
| 2004/0110746 | A1 | 6/2004 | Apodaca et al. |
| 2004/0224968 | A1 | 11/2004 | Seidelmann et al. |
| 2005/0222151 | A1 | 10/2005 | Carruthers et al. |
| 2006/0025404 | A1 | 2/2006 | Ancliff et al. |
| 2006/0052597 | A1 | 3/2006 | Best et al. |
| 2006/0178375 | A1 | 8/2006 | Ohtake et al. |
| 2007/0066821 | A1 | 3/2007 | Allison et al. |
| 2007/0142394 | A1 | 6/2007 | Solomon et al. |
| 2007/0167435 | A1 | 7/2007 | Mutahi et al. |
| 2007/0219240 | A1 | 9/2007 | Cole et al. |
| 2007/0281923 | A1 | 12/2007 | Keith et al. |
| 2008/0045507 | A1 | 2/2008 | Allison et al. |
| 2008/0306066 | A1 | 12/2008 | Carruthers et al. |
| 2009/0131417 | A1 * | 5/2009 | Letavic et al. ................. 514/218 |

FOREIGN PATENT DOCUMENTS

| CA | 1051888 A1 | 4/1979 |
| DE | 817911 | 10/1951 |
| DE | 1902694 A1 | 9/1969 |
| DE | 2514334 A1 | 10/1987 |
| EP | 0089153 A2 | 9/1983 |
| EP | 0134096 A2 | 3/1985 |
| EP | 0143630 A2 | 6/1985 |
| EP | 0488474 A1 | 6/1992 |
| EP | 1388535 A1 | 2/2004 |
| EP | 1396487 A1 | 3/2004 |
| JP | 44-20347 B | 9/1969 |
| JP | 46-37595 B | 11/1971 |
| JP | 6-306051 | 11/1994 |
| JP | 2002 322163 A | 11/2002 |
| WO | WO 84/04304 A1 | 11/1984 |
| WO | WO 00/50391 A1 | 8/2000 |
| WO | WO 00/76984 A2 | 12/2000 |
| WO | WO 01/85715 A2 | 11/2001 |
| WO | WO 03/004480 A2 | 1/2003 |
| WO | WO 03/037869 A1 | 5/2003 |
| WO | WO 03/037891 A1 | 5/2003 |
| WO | WO 03/066604 A2 | 8/2003 |
| WO | WO 03/078398 A1 | 9/2003 |
| WO | WO 03/082205 A2 | 10/2003 |
| WO | WO 03/092686 A1 | 11/2003 |
| WO | WO 2004/018428 A1 | 3/2004 |
| WO | WO 2004/054973 A2 | 7/2004 |
| WO | WO 2005/007644 A1 | 1/2005 |

(Continued)

OTHER PUBLICATIONS

Jantzen and Robinson. Modern Pharmaceutics, 1996, p. 596.*
"Metabolite", http://www.encyclopedia.com/doc/1E1-metabolit. html, accessed Jan. 25, 2008.*
Passani. Trends in Pharmacological Sciences, 2004, 25 (12), 618-625.*
Bundgaard Design of Prodrugs H. Bundgaard Ed Elsevier 1985.
Larsen et al Design and Application of Prodrugs, Drug Design and Development Krogsgaard-Larsen et al Eds Harwood Academic Publishers 1991.
Stahl & Wermuth Handbook of Pharmaceutical Salts, Properties, Selection and Use Stahl and Wermuth Eds Wiley-VCH and VHCA Zurich 2002.

(Continued)

*Primary Examiner* — Noble Jarrell
(74) *Attorney, Agent, or Firm* — Michael J. Atkins

(57) ABSTRACT

Certain cycloalkyloxy- and heterocycloalkyloxypyridine compounds are histamine $H_3$ receptor modulators useful in the treatment of histamine $H_3$ receptor-mediated diseases.

16 Claims, No Drawings

(56) References Cited

FOREIGN PATENT DOCUMENTS

| WO | WO 2005/009976 A1 | 2/2005 |
|---|---|---|
| WO | WO 2005/023247 A1 | 3/2005 |
| WO | WO 2005/040144 A1 | 5/2005 |
| WO | WO 2005 096734 A2 | 10/2005 |
| WO | 2007 009741 A1 | 1/2007 |
| WO | 2007 075629 A2 | 7/2007 |
| WO | WO 2007 075688 A2 | 7/2007 |
| WO | 2007 143422 A2 | 12/2007 |

OTHER PUBLICATIONS

Arrang, J.M. et al.: Auto-inhibition of brain histamine release mediated by a novel class ($H_3$) of histamine receptor; Nature (Apr. 1983) 302: 832-837.
Akhundov, R.A. et al.: "Synthesis and Psychotropic Activity of Amides of 2- aminonicotinic Acid", *Khimiko-Farmatsevticheskki Zhurnal*, vol. 20, No. 1 (1986) pp. 48-50, Rumoscow, Database Beilstein 1993, Database accession No. 5702704 (CNR) BRN: 5598995, 5632883, 5764929, 5774681, (XP002344011).
Ash, A.S.F et al.: Receptors Mediating Some Actions of Histamine. *Br. J. Pharmac. Chemother.* 1966, 27, 427-439.
Bagshawe, K.D.: "Antibody-Directed Enzyme Prodrug Therapy: A Review"; Drug Devel. Research (1995) 34: 220-230.
Barbier, A.J. et al.: Acute wake-promoting actions of JNJ-5207852, a novel, diamine-based H3 antagonist; British J. of Pharmacology (2004) 143: 649-661.
Barnes, J.C. et al.: The Selective Histamine H3 Receptor Antagonist thioperamide Improves Cognition and Enhances Hippocampal Acetylcholine Release in Vivo. Soc. Neurosci. Abstr. (1993) 19: 1813.
Berge, S.M. et al.: "Pharmaceutical Salts"; J. of Pharmaceutical Sciences (1977) 66(1): 1-19.
Bertolini, G. et al.: "A New Rational Hypothesis for the Pharmacophore of the Active Metabolite of Leflunomide, A Potent Immunosuppressive Drug"; J. Med. Chem. (1997) 40: 2011-2016.
Black, J.W. et al.: Definition and Antagonism of Histamine $H_2$-Receptors. *Nature* 1972, 236, 385-390.
Bodor, N.: Novel Approaches to the Design of Safer Drugs: Soft Drugs and Site-Specific Chemical Delivery Systems; Advances in Drug Research (1984) 13: 255-331.
Bodroux Reaction. In Merck Index, $12^{th}$ ed.; Budavari, S., Ed.; Merck & Co., Inc.: Whitehouse Station, NJ, 1996; p. ONR-12.
Bonaventure, P. et al.: "Histamine H3 receptor antagonists: From target identification to drug leads"; Biochem. Pharmacology (2007) 73: 1084-1096.
Buchi, von J. et al.: "Syntheses of Some 2-Dialkylaminoalkoxy-6-alkylaminopyridines and 2-dialkylaminoalkylamino-6-alkoxypyridines", *Helvetica Chimica Acta.*, vol. 48, No. 5 (1965) pp. 1216-1219, Chverlag Helvetica Chimica Acta. Basel, (XP009050917).
Chen, Z.: "Effect of histamine $H_3$-receptor antagonst clobenpropit on spatial memory of radial maze performance in rats"; Acta Pharmacol Sin (2000) 21(10): 905-910.
Fleisher, D. et al.: "Improved oral drug delivery: solubility limitations overcome by the use of prodrugs"; Adv. Drug Del. Rev. (1996) 19: 115-130.
Foks et al.: "Pyrazine derivatives. III. Synthesis and tuberculostatic activity of 6-(N-methyllamino)-pyrazine-2-carboxylic acid derivatives", Polish Journal of Pharmacology and Pharmacy, vol. 26, No. 5 (1974) pp. 537-543 (XP002355523) —Chemical Abstracts, Database accession No. 82:43345 (DN) RN 54409-12-0.
Foks et al.: "Aminomethylation of pyridine- and pyrazinecarbothioamides. V. 6-Chloro- and 6-aminopyrazine-2-carbothioamides in the Mannich reaction", ACTA Poloniae Pharmaceutica, vol. 33, No. 1 (1976) pp. 55-65 (XP002355524) —Chemical Abstracts, Database accession No. 86:72575 (DN).
Fox, G.B. et al.: "Effects of histamine $H_3$ receptor ligands GT-2331 and ciproxifan in a repeated acquisition avoidance response in the spontaneously hypertensive rat pup"; Behavioural Brain Research (2002) 131: 151-161.

Ganellin, C.R. et al.: Synthesis of Potent Non-Imidazole Histamine $H_3$-Receptor Antagonists. *Arch. Pharm. Pharm. Med. Chem.* (Weinheim, Ger.) 1998, 331, 395-404.
Highfield, J.A. et al.: "Preparative, Physico-Chemical and Cytotoxicity Studies of Prodrugs Activated in Hyposiz to Give Metal-Binding Analogues of Bleomycin", *Journal of the Chemical Society*, Perkin Transactions 1, vol. 16 (1999) pp. 2343-2352, GB Chemical Society, Letchworth, (XP002337176).
Ichinose, M. et al.: Histamine $H_3$-Receptors Modulate Nonadrenergic Noncholinergic Neural Bronchoconstriction in Guinea-Pig in Vivo. *Eur. J. Pharmacol.* 1989, 174(1), 49-55.
Imamura, M. et al.: Unmasking of Activated Histamine $H_3$-Receptors in Myocardial Ischemia: Their Role as Regulators of Exocytotic Norepinephrine Release. *J. Pharmacol. Exp. Ther.* 1994, 271(3), 1259-1266.
Krause et al.: "Medicinal Chemistry of Histamine H3 Receptor Agonists"; The Histamine H3 Receptor-A Target for New Drugs; Leurs, R. And Timmerman, H., (Eds.), Elsevier, (1998): 175-196.
Lamberti, C. et al.: "Antidepressant-like effects of endogenous histamine and of two histamine $H_1$ receptor agonists in the mouse forced swim test"; British J. of Pharmacology (1998) 123(7): 1331-1336.
Letavic, M.A. et al.: "Recent Medicinal Chemistry of the Histamine H3 Receptor"; Prog. In Medicinal Chem. (1996)44: 181-206.
Leurs, R. et al.: The Medicinal Chemistry and Therapeutic Potentials of Ligands of the Histamine H3 Receptor; Prog. Drug. Res. (1995) 45: 107-165.
Lin, J-S. et al.: Involvement of Histaminergic Neurons in Arousal Mechanisms Demonstrated with $H_3$-Receptor Ligands in the Cat. *Brain Res.* 1990, 523, 325-330.
Linney, I.D. et al.: Design, Synthesis, and Structure-Activity Relationships of Novel Non-Imidazole Histamine $H_3$ Receptor Antagonists. *J. Med. Chem.* 2000, 43(12), 2362-2370.
Lovenberg, T.W. et al.: Cloning and Functional Expression of the Human Histamine $H_3$ Receptor. *Mol. Pharmacol.* 1999, 55(6), 1101-1107.
MacDonald, S.J.F. et al.: Discovery of Further Pyrrolidine trans-Lactams as Inhibitors of Human Neutrophil Elastase (HNE) with Potential as Development Candidates and the Crystal Structure of HNE Complexed with an Inhibitor (GW475151). *J.Med.Chem.* 2002, 45(18), 3878-3890.
Machidori, H. et al.: Zucker Obese Rats: Defect in Brain Histamine Control of Feeding; Brain Res. (1992) 590: 180-186.
Mase, T. et al.: Synthesis of Muscarinic Receptor Antagonist via a Diastereoselective Michael Reaction, Selective Deoxyfluorination and Metal-Halogen Exchange Reaction. *J. Org. Chem.* 2001, 66, 6775-6786.
McLeod, R.L. et al.: Antimigraine and Sedative Activity of SCH 50971: A Novel Orally-Active Histamine $H_3$ Receptor Agonist. *Soc. Neurosci. Abstr.* 1996, 22, 2010.
Miyazaki, S. et al.: "Effects of Thioperamide on the Cholinergic System and the Step-Through Passive Avoidance Test in Mice"; Meth Find Exp Clin Pharmacol (1995) 17(10): 653-658.
Miyazaki, S. et al.: "Effects of Thioperamide, a Histamine $H_3$-receptor Antagonist, on a Scopolamine-induced Learning Deficit Using an Elevated Plus-maze Test in Mice"; Life Sciences, (1995) 57(23): 2137-2144.
Monti, J.M. et al.: Effects of Selective Activation or Blockade of the Histamine $H_3$ Receptor on Sleep and Wakefulness. *Eur. J. Pharmacol.* 1991, 205(3), 283-287.
Morisset, S. et al.: High Constitutive Activity of Native H3 Receptors Regulates Histamine Neurons in Brain. Nature (Dec. 2000) 408: 860-864.
Orsetti, M. et al.: "Histamine $H_3$-receptor antagonism improves memory retention and reverses the cognitive deficit induced by scopolamine in a two-trial place recognition task"; Elsevier Behavioural Brain Research (2001) 124(2): 235-242.
Ortho-McNeil Pharmaceutical, Inc.: (WO03050099); "Phenylalkynes to Treat Histamine-Mediated Conditions", *Expert Opinion on Therapeutic Patents*, vol. 13, No. 11 (2003) pp. 1759-1762, (XP002337280).
Panula, P. et al.: Significant Changes in the Human Brain Histaminergic System in Alzheimer's Disease. Soc. Neurosci. Abstr. (1995) 21: 1977.

(56) References Cited

OTHER PUBLICATIONS

Patani, G.A. et al.: Bioisosterism: A Rational Approach in Drug Design; Chem. Rev. (1996) 96: 3147-3176.
Pavia et al.: "6-Alkoxy-N,N-disubstituted-2-pyridinamines as Anticonvulsant Agents", Journal of the American Chemical Society, vol. 30, No. 7 (1987) pp. 1210-1214, US American Chemical Society, Washington DC, (XP002337175).
Perez-Garcia, C. et al.: "Effects of histamine $H_3$ receptor ligands in experimental models of anxiety and depression"; Psychopharmacology (1999) 142(2): 215-220.
Phillips, J.G. et al.: Medicinal Chemistry of Histamine $H_3$ Receptor Antagonists. In *The Histamine $H_3$Receptor—A Target for New Drugs.* Leurs, R.; Timmerman, H., Eds.; Elsevier: 1998; pp. 197-222.
Reiner, J.E. et al.: Non-Covalent Thrombin Inhibitors Featuring $P_3$-Heterocycles with $P_1$-Monocyclic Arginine Surrogates. *Bioorg. Med. Chem. Lett.* 2002, 12, 1203-1208.
Robinson, R.P. et al.: "Discovery of the Hemifumarate and (α-L-Alanyloxy)methyl Ether as Prodrugs of an Antirheumatic Oxindole: Prodrugs for the Enolic OH Group"; J. Med. Chem. (1996) 39: 10-18.
Schlicker, E. et al.: The Moderate Affinity of Clozapine at H3 Receptors Is Not Shared by Its Two Major Metabolites and by Structurally Related and Unrelated Atypical Neuroleptics. Naunyn-Schmiedeberg's Arch. Pharmacol. (1996) 353: 290-294.
Searles, Jr., S. et al.: β-Priopiolactam and the Use of Mesityl Grignard Reagent in the Breckpot β-Lactam Syntheses. Chem. Ind. (London) 1964, 51, 2097.
Shan, D. et al.: "Prodrug Strategies Based on Intramolecular Cyclization Reactions"; J. of Pharm. Sciences (Jul. 1997) 86(7): 765-767.
Shono, T. et al.: Electroorganic Chemistry. 82. β-Amino Acid Esters from α-Methoxycarbamates and Ketene Silyl Acetals; Cyclization to β-Lactams. J. Org. Chem. 1984, 49, 1056-1059.
Stark, H.: "Recent Advances in Histamine $H_3/H_4$ Receptor Ligands", *Expert Opinion on Therapeutic Patents*, vol. 13, No. 6 (2003) pp. 851-865, Ashley Publications, GB, ISSN: 1354-3776, (XP002298271).
Stark, H. et al.: Developments of Histamine H3-Receptor Antagonists. Drugs Future (1996) 21(5): 507-520.
Thunus et al.: "Quelques Derives de la (Methyl-4, Peperazinyl-1)-2 Pyridine Substituee en 3", *European Journal of Medicinal Chemistry*, vol. 9, No. 1 (1974) pp. 55-58, Freditions Scientifique Elsevier, Paris, (XP009050898).
Tozer, M.J. et al.: Histamine $H_3$ Receptor Antagonists. *Exp. Opin. Ther. Patents* 2000, 10(7), 1045-1055.
Turner, S.C. et al.: A New Class of Histamine $H_3$-Receptor Antagonists: Synthesis and Structure-Activity Relationships of 7,8,9,10-Tetrahydro-6H-cyclohepta[b]quinolones. *Bioorg. Med. Chem. Lett.* 2003, 13(13), 2131-2135.
Vippagunta, S. R. et al: "Crystalline solids"; Advanced Drug Delivery Reviews (2001) 48: 3-26.
Walczynski, K. et al.: Non-Imidazole Histamine $H_3$ Ligands. Part I. Synthesis of 2-(1-Piperazinyl)- and 2-(Hexahydro-1H-1,4-diazepin-1-yl)benzothiazole Derivatives as $H_3$-Antagonists with $H_1$ Blocking Activities. *Farmaco* 1999, 54, 684-694.
Walczynski, K. et al.: Non-Imidazole Histamine H3 Ligands, Part 2: New 2-Substituted Benzothiazoles as Histamine $H_3$ Antagonists. Arch. Pharm. Pharm. Med. Chem. (Weinheim, Ger.) 1999, 332, 389-398.
Yokoyama, H. et al.: Effect of Thioperamide, a Histamine $H_3$ Receptor Antagonist, on Electrically Induced Convulsions in Mice. Eur. J. Pharmacol. (1993) 234: 129-133.
Search Report and Written Opinion for corresponding Singapore Serial No. 201003459.3 mailed on Sep. 6, 2011.
TIPO's Search Report for ROC Patent Application No. 097144606 mailed Aug. 5, 2013, 1 page.

\* cited by examiner

CYCLOALKYLOXY- AND HETEROCYCLOALKYLOXYPYRIDINE COMPOUNDS AS MODULATORS OF THE HISTAMINE H₃ RECEPTOR

CROSS REFERENCE TO RELATED APPLICATIONS

This application claims the benefit of U. S. Provisional Application 60/989,246, filed on Nov. 20, 2007, which is incorporated by reference herein in its entirety.

FIELD OF THE INVENTION

The present invention relates to certain cycloalkyloxy- and heterocycloalkyloxypyridine compounds, pharmaceutical compositions containing them, and methods of using them for the treatment of disease states, disorders, and conditions mediated by the histamine $H_3$ receptor.

BACKGROUND OF THE INVENTION

The histamine $H_3$ receptor was first described as a presynaptic autoreceptor in the central nervous system (CNS) (Arrang, J.-M. et al. Nature 1983, 302, 832-837) controlling the synthesis and release of histamine. The histamine $H_3$ receptor is primarily expressed in the mammalian central nervous system (CNS), with some minimal expression in peripheral tissues such as vascular smooth muscle.

Thus, several indications for histamine $H_3$ antagonists and inverse agonists have been proposed based on animal pharmacology and other experiments with known histamine $H_3$ antagonists (e.g. thioperamide). (See: Krause et al. and Phillips et al. in "The Histamine $H_3$ Receptor-A Target for New Drugs", Leurs, R. and Timmerman, H., (Eds.), Elsevier, 1998, pp. 175-196 and 197-222; Morisset, S. et al. Nature 2000, 408, 860-864.) These include conditions such as cognitive disorders, sleep disorders, psychiatric disorders, and other disorders.

For example, histamine $H_3$ antagonists have been shown to have pharmacological activity relevant to several key symptoms of depression, including sleep disorders (e.g. sleep disturbances, fatigue, and lethargy) and cognitive difficulties (e.g. memory and concentration impairment), as described above. For reviews, see: Bonaventure, P. et al. Biochem. Pharm. 2007, 73, 1084-1096; Letavic, M. A. et al. Prog. Med. Chem. 1996, 44, 181-206. There remains a need for potent histamine $H_3$ receptor modulators with desirable pharmaceutical properties.

Various literature publications describe small-molecule histamine $H_3$ receptor inhibitors: PCT Intl. Appl. Publ. WO 2005/040144 (diazepanyl derivatives); U.S. Pat. Appl. Publ. US 2007/0167435 (phenoxypiperidines); U.S. Pat. Appl. Publ. US 2005/222151 (non-imidazole heterocyclic compounds); U.S. Pat. Appl. Publ. US 2007/219240 (N-substituted-azacyclylamines); U.S. Pat. Appl. Publ. US 2006/0052597 (aryloxyalkylamine derivatives); U.S. Pat. Appl. Publ. US 2006/0178375 (heteroaryloxy nitrogen-containing derivatives); U.S. Pat. Appl. 11/753,607; and U.S. patent application Ser. No. 11/766,144.

SUMMARY OF THE INVENTION

Certain cycloalkyloxy- and heterocycloalkyloxypyridine derivatives have now been found to have histamine $H_3$ receptor modulating activity. Thus, the invention is directed to the general and preferred embodiments defined, respectively, by the independent and dependent claims appended hereto, which are incorporated by reference herein.

In one general aspect the invention relates to a compound of the following Formula (I):

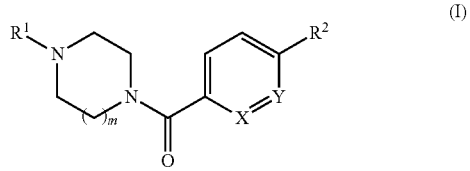

wherein
$R^1$ is —$C_{1-5}$alkyl or a saturated cycloalkyl group;
m is 1 or 2;
$R^2$ is —H or —$OCHR^3R^4$;
  where $R^3$ is —H; and
  $R^4$ is a cycloalkyl or heterocycloalkyl ring, unsubstituted or substituted with —$C_{1-4}$alkyl or acetyl;
  or, $R^3$ and $R^4$ taken together with the carbon to which they are attached form a cycloalkyl or heterocycloalkyl ring, unsubstituted or substituted with —$C_{1-4}$alkyl or acetyl;
X is N or CH; and
Y is N or $CR^a$;
  where $R^a$ is —H, —$OCHR^3R^4$, —$CH_2NR^bR^c$, —CN, —$CO_2C_{1-4}$alkyl, —$CO_2H$, or —$CONR^bR^c$;
  $R^b$ and $R^c$ are each independently —H or —$C_{1-4}$alkyl;
with the proviso that one of X and Y is N and one of $R^2$ and $R^a$ is —$OCHR^3R^4$;
or a pharmaceutically acceptable salt, a pharmaceutically acceptable prodrug, or a pharmaceutically active metabolite thereof.

In a further general aspect, the invention relates to pharmaceutical compositions each comprising: (a) an effective amount of a compound of Formula (I), or a pharmaceutically acceptable salt, pharmaceutically acceptable prodrug, or pharmaceutically active metabolite thereof; and (b) a pharmaceutically acceptable excipient.

In another general aspect, the invention is directed to a method of treating a subject suffering from or diagnosed with a disease, disorder, or medical condition mediated by histamine $H_3$ receptor activity, comprising administering to the subject in need of such treatment an effective amount of a compound of Formula (I), or a pharmaceutically acceptable salt, pharmaceutically acceptable prodrug, or pharmaceutically active metabolite thereof.

In certain preferred embodiments of the inventive method, the disease, disorder, or medical condition is selected from: cognitive disorders, sleep disorders, psychiatric disorders, and other disorders.

Additional embodiments, features, and advantages of the invention will be apparent from the following detailed description and through practice of the invention.

DETAILED DESCRIPTION

The invention may be more fully appreciated by reference to the following description, including the following glossary of terms and the concluding examples. For the sake of brevity, the disclosures of the publications, including patents, cited in this specification are herein incorporated by reference.

As used herein, the terms "including", "containing" and "comprising" are used herein in their open, non-limiting sense.

The term "alkyl" refers to a straight- or branched-chain alkyl group having from 1 to 12 carbon atoms in the chain. Examples of alkyl groups include methyl (Me, which also may be structurally depicted by a bond "/"), ethyl (Et), n-propyl, isopropyl (iPr), butyl (Bu or n-Bu), isobutyl (iBu), sec-butyl, tert-butyl (t-Bu), pentyl, isopentyl, tert-pentyl, hexyl, isohexyl, and groups that in light of the ordinary skill in the art and the teachings provided herein would be considered equivalent to any one of the foregoing examples.

The term "cycloalkyl" refers to a saturated or partially saturated, monocyclic carbocycle having from 3 to 10 ring atoms per carbocycle. Illustrative examples of cycloalkyl groups include the following entities, in the form of properly bonded moieties:

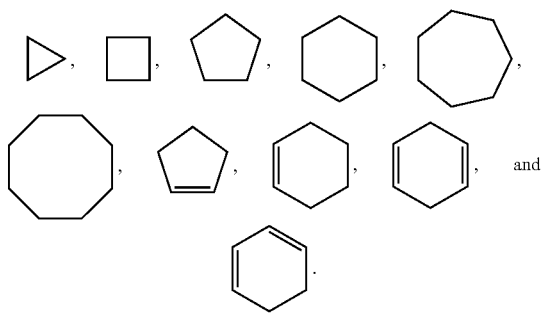

A "heterocycloalkyl" refers to a monocyclic ring structure that is saturated or partially saturated and has from 4 to 7 ring atoms per ring structure selected from carbon atoms and up to two heteroatoms selected from nitrogen, oxygen, and sulfur. The ring structure may optionally contain up to two oxo groups on sulfur ring members. Illustrative entities, in the form of properly bonded moieties, include:

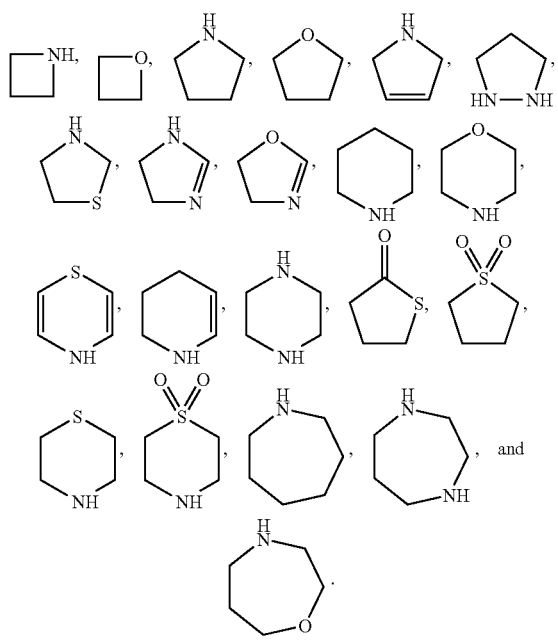

The term "heteroaryl" refers to a monocyclic, fused bicyclic, or fused polycyclic aromatic heterocycle (ring structure having ring atoms selected from carbon atoms and up to four heteroatoms selected from nitrogen, oxygen, and sulfur) having from 3 to 12 ring atoms per heterocycle. Illustrative examples of heteroaryl groups include the following entities, in the form of properly bonded moieties:

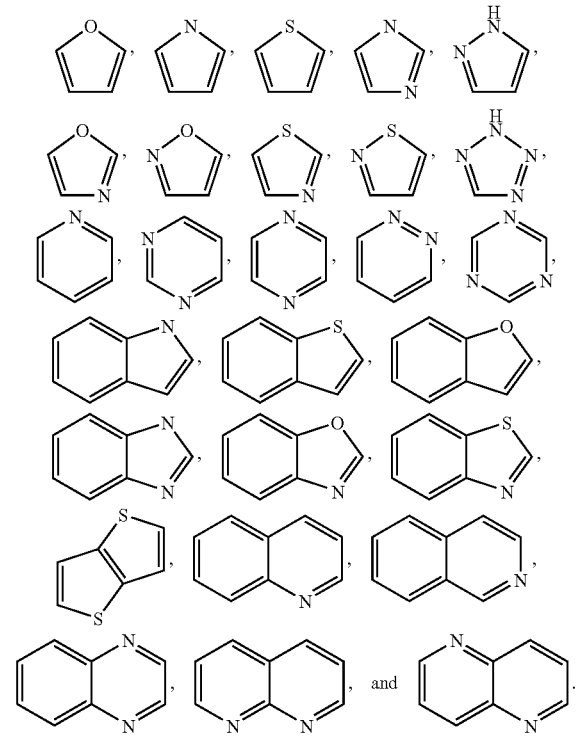

Those skilled in the art will recognize that the species of cycloalkyl, heterocycloalkyl, and heteroaryl groups listed or illustrated above are not exhaustive, and that additional species within the scope of these defined terms may also be selected.

The term "halogen" represents chlorine, fluorine, bromine or iodine. The term "halo" represents chloro, fluoro, bromo or iodo.

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system. In cases where a specified moiety or group is not expressly noted as being optionally substituted or substituted with any specified substituent, it is understood that such a moiety or group is intended to be unsubstituted.

Any formula given herein is intended to represent compounds having structures depicted by the structural formula as well as certain variations or forms. In particular, compounds of any formula given herein may have asymmetric centers and therefore exist in different enantiomeric forms. All optical isomers and stereoisomers of the compounds of the general formula, and mixtures thereof, are considered within the scope of the formula. Thus, any formula given herein is intended to represent a racemate, one or more enantiomeric forms, one or more diastereomeric forms, one or more atropisomeric forms, and mixtures thereof. Further-more, certain structures may exist as geometric isomers (i.e., cis and trans isomers), as tautomers, or as atropisomers. Additionally, any formula given herein is intended to embrace hydrates, solvates, and polymorphs of such compounds, and mixtures thereof.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, chlorine, and iodine, such as $^{2}H$, $^{3}H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$, $^{125}I$, respectively. Such isotopically labeled compounds are useful in metabolic studies (preferably with $^{14}C$), reaction kinetic studies (with, for example $^{2}H$ or $^{3}H$), detection or imaging techniques [such as positron emission tomography (PET) or single-photon emission computed tomography (SPECT)] including drug or substrate tissue distribution assays, or in radioactive treatment of patients. In particular, an $^{18}F$ or $^{11}C$ labeled compound may be particularly preferred for PET or SPECT studies. Further, substitution with heavier isotopes such as deuterium (i.e., $^{2}H$) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

When referring to any formula given herein, the selection of a particular moiety from a list of possible species for a specified variable is not intended to define the moiety for the variable appearing elsewhere. In other words, where a variable appears more than once, the choice of the species from a specified list is independent of the choice of the species for the same variable elsewhere in the formula.

In preferred embodiments of Formula (I), $R^1$ is isopropyl, cyclopropyl, cyclobutyl, or cyclopentyl. In other preferred embodiments, $R^1$ is cyclopropyl or cyclobutyl.

In some embodiments, m is 1. In other embodiments, m is 2.

In some embodiments, X is N. In other embodiments, Y is N.

In some embodiments, $R^2$ is —H and $R^a$ is —OCHR$^3$R$^4$. In other embodiments, $R^2$ is —OCHR$^3$R$^4$ and $R^a$ is not —OCHR$^3$R$^4$.

In some embodiments, $R^3$ is —H and $R^4$ is cyclopropyl, cyclocyclobutyl, or 3-methyl-oxetan-3-yl. In other embodiments, $R^3$ and $R^4$ taken together with the carbon to which they are attached form cyclobutyl, cyclopentyl, cyclohexyl, tetrahydrofuranyl, tetrahydropyranyl, oxepanyl, tetrahydrothiophenyl, tetrahydrothiopyranyl, pyrrolidinyl, thiepanyl, piperidinyl, or azepanyl, unsubstituted or substituted with methyl, ethyl, isopropyl, or acetyl.

In still other embodiments, —OCHR$^3$R$^4$ is tetrahydro-furan-3-yloxy, 3-methyl-oxetan-3-ylmethoxy, cyclopentyloxy, cyclohexyloxy, tetrahydro-pyran-4-yloxy, tetrahydro-pyran-3-yloxy, cyclobutyloxy, oxepan-4-yloxy, oxepan-3-yloxy, cyclobutyl methoxy, cyclopropyl methoxy, tetrahydro-thiophen-3-yloxy, tetrahydro-thiopyran-4-yloxy, 1-methyl-pyrrolidin-3-yloxy, 1-acetyl-pyrrolidin-3-yloxyl, thiepan-3-yloxy, thiepan-4-yloxy, 1-methyl-piperidin-4-yloxy, 1-acetyl-piperidin-4-yloxy, 1-isopropyl-azepan-4-yloxy, 1-acetyl-azepan-4-yloxy, 1-ethyl-azepan-3-yloxy, or 1-acetyl-azepan-3-yloxy. In still other embodiments, —OCHR$^3$R$^4$ is tetrahydro-furan-3-yloxy, 3-methyl-oxetan-3-ylmethoxy, cyclopentyloxy, cyclohexyloxy, or tetrahydro-pyran-4-yloxy.

In further preferred embodiments, —OCHR$^3$R$^4$ is tetrahydro-pyran-4-yloxy and m is 2.

In certain preferred embodiments, the compound of Formula (I) is selected from the group consisting of:

| Ex. | Chemical Name |
|---|---|
| 1 | (4-Isopropyl-piperazin-1-yl)-[6-(tetrahydro-furan-3-yloxy)-pyridin-3-yl]-methanone; |
| 2 | (4-Isopropyl-[1,4]diazepan-1-yl)-[6-(tetrahydro-furan-3-yloxy)-pyridin-3-yl]-methanone; |
| 3 | (4-Cyclopropyl-[1,4]diazepan-1-yl)-[6-(tetrahydro-furan-3-yloxy)-pyridin-3-yl]-methanone; |
| 4 | (4-Cyclobutyl-[1,4]diazepan-1-yl)-[6-(tetrahydro-furan-3-yloxy)-pyridin-3-yl]-methanone; |
| 5 | (4-Isopropyl-piperazin-1-yl)-[6-(3-methyl-oxetan-3-ylmethoxy)-pyridin-3-yl]-methanone; |
| 6 | (4-Isopropyl-[1,4]diazepan-1-yl)-[6-(3-methyl-oxetan-3-ylmethoxy)-pyridin-3-yl]-methanone; |
| 7 | (4-Cyclobutyl-[1,4]diazepan-1-yl)-(6-cyclopentyloxy-pyridin-3-yl)-methanone; |
| 8 | (4-Cyclobutyl-[1,4]diazepan-1-yl)-(6-cyclohexyloxy-pyridin-3-yl)-methanone; |
| 9 | (4-Cyclobutyl-[1,4]diazepan-1-yl)-[6-(tetrahydro-pyran-4-yloxy)-pyridin-3-yl]-methanone; |
| 10 | 6-(4-Cyclopropyl-[1,4]diazepane-1-carbonyl)-3-(tetrahydro-furan-3-yloxy)-pyridine-2-carbonitrile; |
| 11 | 3-Cyclopentyloxy-6-(4-cyclopropyl-[1,4]diazepane-1-carbonyl)-pyridine-2-carbonitrile; |
| 12 | 3-Cyclohexyloxy-6-(4-cyclopropyl-[1,4]diazepane-1-carbonyl)-pyridine-2-carbonitrile; |
| 13 | (4-Isopropyl-[1,4]diazepan-1-yl)-[6-(tetrahydro-pyran-4-yloxy)-pyridin-3-yl]-methanone; |
| 14 | (4-Cyclopropyl-[1,4]diazepan-1-yl)-[6-(tetrahydro-pyran-4-yloxy)-pyridin-3-yl]-methanone; |
| 15 | (4-Cyclopentyl-[1,4]diazepan-1-yl)-[6-(tetrahydro-pyran-4-yloxy)-pyridin-3-yl]-methanone; |
| 16 | (4-Isopropyl-piperazin-1-yl)-[6-(tetrahydro-pyran-4-yloxy)-pyridin-3-yl]-methanone; |

| Ex. | Chemical Name |
|---|---|
| 17 | (4-Cyclopropyl-piperazin-1-yl)-[6-(tetrahydro-pyran-4-yloxy)-pyridin-3-yl]-methanone; |
| 18 | (4-Cyclobutyl-piperazin-1-yl)-[6-(tetrahydro-pyran-4-yloxy)-pyridin-3-yl]-methanone; |
| 19 | (4-Cyclopentyl-piperazin-1-yl)-[6-(tetrahydro-pyran-4-yloxy)-pyridin-3-yl]-methanone; |
| 20 | (4-Cyclobutyl-[1,4]diazepan-1-yl)-[5-(tetrahydro-pyran-4-yloxy)-pyridin-2-yl]-methanone; |
| 21 | (4-Cyclobutyl-[1,4]diazepan-1-yl)-[6-(tetrahydro-pyran-4-yloxy)-pyridin-2-yl]-methanone; |
| 22 | (6-Cyclobutoxy-pyridin-3-yl)-(4-cyclobutyl-[1,4]diazepan-1-yl)-methanone; |
| 23 | (4-Cyclobutyl-[1,4]diazepan-1-yl)-[6-(oxepan-4-yloxy)-pyridin-3-yl]-methanone; |
| 24 | (4-Cyclobutyl-[1,4]diazepan-1-yl)-[6-(oxepan-3-yloxy)-pyridin-3-yl]-methanone; |
| 25 | (4-Cyclobutyl-[1,4]diazepan-1-yl)-(6-cyclobutylmethoxy-pyridin-3-yl)-methanone; |
| 26 | (4-Cyclobutyl-[1,4]diazepan-1-yl)-(6-cyclopropylmethoxy-pyridin-3-yl)-methanone; |
| 27 | (4-Cyclobutyl-[1,4]diazepan-1-yl)-[6-(tetrahydro-thiophen-3-yloxy)-pyridin-3-yl]-methanone; |
| 28 | (4-Cyclobutyl-[1,4]diazepan-1-yl)-[6-(tetrahydro-thiopyran-4-yloxy)-pyridin-3-yl]-methanone; |
| 29 | (4-Cyclobutyl-[1,4]diazepan-1-yl)-[6-(1-methyl-pyrrolidin-3-yloxy)-pyridin-3-yl]-methanone; |
| 30 | 1-{3-[5-(4-Cyclobutyl-[1,4]diazepane-1-carbonyl)-pyridin-2-yloxy]-pyrrolidin-1-yl}-ethanone; |
| 31 | (4-Cyclobutyl-[1,4]diazepan-1-yl)-[6-(thiepan-3-yloxy)-pyridin-3-yl]-methanone; |
| 32 | (4-Cyclobutyl-[1,4]diazepan-1-yl)-[6-(thiepan-4-yloxy)-pyridin-3-yl]-methanone; |
| 33 | (4-Cyclobutyl-[1,4]diazepan-1-yl)-[6-(1-methyl-piperidin-4-yloxy)-pyridin-3-yl]-methanone; |
| 34 | 1-{4-[5-(4-Cyclobutyl-[1,4]diazepane-1-carbonyl)-pyridin-2-yloxy]-piperidin-1-yl}-ethanone; |
| 35 | (4-Cyclobutyl-[1,4]diazepan-1-yl)-[6-(1-isopropyl-azepan-4-yloxy)-pyridin-3-yl]-methanone; |
| 36 | 1-{4-[5-(4-Cyclobutyl-[1,4]diazepane-1-carbonyl)-pyridin-2-yloxy]-azepan-1-yl}-ethanone; |
| 37 | (4-Cyclobutyl-[1,4]diazepan-1-yl)-[6-(1-ethyl-azepan-3-yloxy)-pyridin-3-yl]-methanone; and |
| 38 | 1-{3-[5-(4-Cyclobutyl-[1,4]diazepane-1-carbonyl)-pyridin-2-yloxy]-azepan-1-yl}-ethanone; and |
| 39 | (4-Cyclopropyl-piperazin-1-yl)-[6-(tetrahydro-pyran-3-yloxy)-pyridin-3-yl]-methanone; |
| 40 | (4-Cyclobutyl-[1,4]diazepan-1-yl)-[6-(tetrahydro-pyran-4-yloxy)-pyridin-3-yl]-methanone•HCl | and pharmaceutically acceptable salts thereof.

The invention includes also pharmaceutically acceptable salts of the compounds of Formula (I), preferably of those described above and of the specific compounds exemplified herein, and methods of treatment using such salts.

A "pharmaceutically acceptable salt" is intended to mean a salt of a free acid or base of a compound represented by Formula (I) that is non-toxic, biologically tolerable, or otherwise biologically suitable for administration to the subject. See, generally, S. M. Berge, et al., "Pharmaceutical Salts", J. Pharm. Sci., 1977, 66:1-19, and *Handbook of Pharmaceutical Salts, Properties, Selection, and Use*, Stahl and Wermuth, Eds., Wiley-VCH and VHCA, Zurich, 2002. Examples of pharmaceutically acceptable salts are those that are pharmacologically effective and suitable for contact with the tissues of patients without undue toxicity, irritation, or allergic response.

A compound of Formula (I) may possess a sufficiently acidic group, a sufficiently basic group, or both types of functional groups, and accordingly react with a number of inorganic or organic bases, and inorganic and organic acids, to form a pharmaceutically acceptable salt. Examples of pharmaceutically acceptable salts include sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

If the compound of Formula (I) contains a basic nitrogen, the desired pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, ethanesulfonic acid, any compatible mixture of acids such as those given as examples herein, and any other acid and mixture thereof that are regarded as equivalents or acceptable substitutes in light of the ordinary level of skill in this technology.

If the compound of Formula (I) is an acid, such as a carboxylic acid or sulfonic acid, the desired pharmaceutically acceptable salt may be prepared by any suitable method, for example, treatment of the free acid with an inorganic or organic base, such as an amine (primary, secondary or tertiary), an alkali metal hydroxide, alkaline earth metal hydroxide, any compatible mixture of bases such as those given as examples herein, and any other base and mixture thereof that are regarded as equivalents or acceptable substitutes in light of the ordinary level of skill in this technology. Illustrative examples of suitable salts include organic salts derived from amino acids, such as glycine and arginine, ammonia, carbonates, bicarbonates, primary, secondary, and tertiary amines, and cyclic amines, such as benzylamines, pyrrolidines, piperidine, morpholine, and piperazine, and inorganic salts derived from sodium, calcium, potassium, magnesium, manganese, iron, copper, zinc, aluminum, and lithium.

The invention also relates to pharmaceutically acceptable prodrugs of the compounds of Formula (I), and treatment methods employing such pharmaceutically acceptable prodrugs. The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of Formula (I)). A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, for example, in "Design of Prodrugs", ed. H. Bundgaard, Elsevier, 1985.

Examples of prodrugs include compounds having an amino acid residue, or a polypeptide chain of two or more (e.g., two, three or four) amino acid residues, covalently joined through an amide or ester bond to a free amino, hydroxy, or carboxylic acid group of a compound of Formula (I). Examples of amino acid residues include the twenty naturally occurring amino acids, commonly designated by three letter symbols, as well as 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone.

Additional types of prodrugs may be produced, for instance, by derivatizing free carboxyl groups of structures of Formula (I) as amides or alkyl esters. Examples of amides include those derived from ammonia, primary $C_{1-6}$alkyl amines and secondary di($C_{1-6}$alkyl) amines. Secondary amines include 5- or 6-membered heterocycloalkyl or heteroaryl ring moieties. Examples of amides include those that are derived from ammonia, $C_{1-3}$alkyl primary amines, and di($C_{1-2}$ alkyl)amines. Examples of esters of the invention include $C_{1-7}$alkyl, $C_{5-7}$cycloalkyl, phenyl, and phenyl($C_{1-6}$ alkyl) esters. Preferred esters include methyl esters. Prodrugs may also be prepared by derivatizing free hydroxy groups using groups including hemisuccinates, phosphate esters, dimethylaminoacetates, and phosphoryloxymethyloxycarbonyls, following procedures such as those outlined in *Adv. Drug Delivery Rev.* 1996, 19, 115. Carbamate derivatives of hydroxy and amino groups may also yield prodrugs. Carbonate derivatives, sulfonate esters, and sulfate esters of hydroxy groups may also provide prodrugs. Derivatization of hydroxy groups as (acyloxy)methyl and (acyloxy)ethyl ethers, wherein the acyl group may be an alkyl ester, optionally substituted with one or more ether, amine, or carboxylic acid functionalities, or where the acyl group is an amino acid ester as described above, is also useful to yield prodrugs. Prodrugs of this type may be prepared as described in *J. Med. Chem.* 1996, 39, 10. Free amines can also be derivatized as amides, sulfonamides or phosphonamides. All of these prodrug moieties may incorporate groups including ether, amine, and carboxylic acid functionalities.

The present invention also relates to pharmaceutically active metabolites of the compounds of Formula (I), which may also be used in the methods of the invention. A "pharmaceutically active metabolite" means a pharmacologically active product of metabolism in the body of a compound of Formula (I) or salt thereof. Prodrugs and active metabolites of a compound may be determined using routine techniques known or available in the art. See, e.g., Bertolini et al., *J. Med. Chem.* 1997, 40, 2011-2016; Shan et al., *J. Pharm. Sci.* 1997, 86 (7), 765-767; Bagshawe, *Drug Dev. Res.* 1995, 34, 220-230; Bodor, *Adv. Drug Res.* 1984, 13, 224-331; Bundgaard, Design of Prodrugs (Elsevier Press, 1985); and Larsen, Design and Application of Prodrugs, Drug Design and Development (Krogsgaard-Larsen, et al., eds., Harwood Academic Publishers, 1991).

The compounds of Formula (I) and their pharmaceutically acceptable salts, pharmaceutically acceptable prodrugs, and pharmaceutically active metabolites of the present invention are useful as modulators of the histamine $H_3$ receptor in the methods of the invention. As such modulators, the compounds may act as antagonists, agonists, or inverse agonists. "Modulators" include both inhibitors and activators, where "inhibitors" refer to compounds that decrease, prevent, inactivate, desensitize or down-regulate histamine $H_3$ receptor expression or activity, and "activators" are compounds that increase, activate, facilitate, sensitize, or up-regulate histamine $H_3$ receptor expression or activity.

The term "treat" or "treating" as used herein is intended to refer to administration of an active agent or composition of the invention to a subject for the purpose of effecting a therapeutic or prophylactic benefit through modulation of histamine $H_3$ receptor activity. Treating includes reversing, ameliorating, alleviating, inhibiting the progress of, lessening the severity of, or preventing a disease, disorder, or condition, or one or more symptoms of such disease, disorder or condition mediated through modulation of histamine $H_3$ receptor activity. The term "subject" refers to a mammalian patient in need of such treatment, such as a human.

Accordingly, the invention relates to methods of using the compounds described herein to treat subjects diagnosed with or suffering from a disease, disorder, or condition mediated by histamine $H_3$ receptor activity, such as: cognitive disorders, sleep disorders, psychiatric disorders, and other disorders. Symptoms or disease states are intended to be included within the scope of "medical conditions, disorders, or diseases."

Cognitive disorders include, for example, dementia, Alzheimer's disease (Panula, P. et al., Soc. Neurosci. Abstr. 1995, 21, 1977), cognitive dysfunction, mild cognitive impairment (pre-dementia), attention deficit hyperactivity disorders (ADHD), attention-deficit disorders, and learning and memory disorders (Barnes, J. C. et al., Soc. Neurosci. Abstr. 1993, 19, 1813). Learning and memory disorders include, for example, learning impairment, memory impairment, age-related cognitive decline, and memory loss. $H_3$ antagonists have been shown to improve memory in a variety of memory tests, including the elevated plus maze in mice (Miyazaki, S. et al. Life Sci. 1995, 57(23), 2137-2144), a two-trial place recognition task (Orsetti, M. et al. Behav. Brain Res. 2001, 124(2), 235-242), the passive avoidance test in mice (Miyazaki, S. et al. Meth. Find. Exp. Clin. Pharmacol. 1995, 17(10), 653-658) and the radial maze in rats (Chen, Z. Acta Pharmacol. Sin. 2000, 21(10), 905-910). Also, in the spontaneously hypertensive rat, an animal model for the learning impairments in attention-deficit disorders, $H_3$ antagonists were shown to improve memory (Fox, G. B. et al. Behav. Brain Res. 2002, 131(1-2), 151-161).

Sleep disorders include, for example, insomnia, disturbed sleep, narcolepsy (with or without associated cataplexy), cataplexy, disorders of sleep/wake homeostasis, idiopathic somnolence, excessive daytime sleepiness (EDS), circadian rhythm disorders, fatigue, lethargy, jet lag (phase delay), and REM-behavioral disorder. Fatigue and/or sleep impairment may be caused by or associated with various sources, such as, for example, sleep apnea, perimenopausal hormonal shifts, Parkinson's disease, multiple sclerosis (MS), depression, chemotherapy, or shift work schedules.

Psychiatric disorders include, for example, schizophrenia (Schlicker, E. and Marr, I., Naunyn-Schmiedeberg's Arch. Pharmacol. 1996, 353, 290-294), including cognitive deficits and negative symptoms associated with schizophrenia, bipolar disorders, manic disorders, depression (Lamberti, C. et al. Br. J. Pharmacol. 1998, 123(7), 1331-1336; Perez-Garcia, C. et al. Psychopharmacology 1999, 142(2), 215-220) (Also see: Stark, H. et al., Drugs Future 1996, 21(5), 507-520; and Leurs, R. et al., Prog. Drug Res. 1995, 45, 107-165 and references cited therein.), including bipolar depression, obsessive-compulsive disorder, and post-traumatic stress disorder.

Other disorders include, for example, motion sickness, vertigo (e.g. vertigo or benign postural vertigo), tinitus, epilepsy (Yokoyama, H. et al., Eur. J. Pharmacol. 1993, 234, 129-133), migraine, neurogenic inflammation, neuropathic pain, Down Syndrome, seizures, eating disorders (Machidori, H. et al., Brain Res. 1992, 590, 180-186), obesity, substance abuse disorders, movement disorders (e.g. restless legs syndrome), and eye-related disorders (e.g. macular degeneration and retinitis pigmentosis).

Particularly, as modulators of the histamine $H_3$ receptor, the compounds of the present invention are useful in the treatment or prevention of depression, disturbed sleep, narcolepsy, fatigue, lethargy, cognitive impairment, memory impairment, memory loss, learning impairment, attention-deficit disorders, and eating disorders.

In treatment methods according to the invention, an effective amount of at least one compound according to the invention is administered to a subject suffering from or diagnosed as having such a disease, disorder, or condition. An "effective amount" means an amount or dose sufficient to generally bring about the desired therapeutic or prophylactic benefit in patients in need of such treatment for the designated disease, disorder, or condition. Effective amounts or doses of the compounds of the present invention may be ascertained by routine methods such as modeling, dose escalation studies or clinical trials, and by taking into consideration routine factors, e.g., the mode or route of administration or drug delivery, the pharmacokinetics of the compound, the severity and course of the disease, disorder, or condition, the subject's previous or ongoing therapy, the subject's health status and response to drugs, and the judgment of the treating physician. An example of a dose is in the range of from about 0.001 to about 200 mg of compound per kg of subject's body weight per day, preferably about 0.01 to 100 mg/kg/day, or about 1 to 35 mg/kg/day, in single or divided dosage units (e.g., BID, TID, QID). For a 70-kg human, an illustrative range for a suitable dosage amount is from about 0.05 to about 7 g/day, or about 0.2 to about 2.5 g/day.

Once improvement of the patient's disease, disorder, or condition has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms.

In addition, the compounds of the invention may be used in combination with additional active ingredients in the treatment of the above conditions. In an exemplary embodiment, additional active ingredients are those that are known or discovered to be effective in the treatment of conditions, disorders, or diseases mediated by histamine $H_3$ receptor activity or that are active against another target associated with the particular condition, disorder, or disease, such as $H_1$ receptor antagonists, $H_2$ receptor antagonists, $H_4$ receptor antagonists, topiramate, and neurotransmitter modulators such as serotonin-norepinephrine reuptake inhibitors, selective serotonin reuptake inhibitors (SSRIs), noradrenergic reuptake inhibitors, non-selective serotonin re-uptake inhibitors (NSSRIs), acetylcholinesterase inhibitors (such as tetrahydroaminoacridine, donepezil, rivastigmine, or galantamine), or modafinil. The combination may serve to increase efficacy (e.g., by including in the combination a compound potentiating the potency or effectiveness of a compound according to the invention), decrease one or more side effects, or decrease the required dose of the compound according to the invention.

More particularly, compounds of the invention in combination with modafinil are useful for the treatment of narcolepsy, excessive daytime sleepiness (EDS), Alzheimer's disease, depression, attention-deficit disorders, MS-related fatigue, post-anesthesia grogginess, cognitive impairment, schizophrenia, spasticity associated with cerebral palsy, age-related memory decline, idiopathic somnolence, or jet-lag. Preferably, the combination method employs doses of modafinil in the range of about 20 to 300 mg per dose.

In another embodiment, compounds of the invention in combination with topiramate are useful for the treatment of obesity. Preferably, the combination method employs doses of topiramate in the range of about 20 to 300 mg per dose.

The compounds of the invention are used, alone or in combination with one or more other active ingredients, to formulate pharmaceutical compositions of the invention. A pharmaceutical composition of the invention comprises: (a) an effective amount of a compound of Formula (I), or a pharmaceutically acceptable salt, pharmaceutically acceptable prodrug, or pharmaceutically active metabolite thereof; and (b) a pharmaceutically acceptable excipient.

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of a compound of the invention and that is compatible therewith. Examples of excipients include calcium carbonate, calcium phosphate, various sugars and types of starch, cellulose derivatives, gelatin, vegetable oils, and polyethylene glycols.

Delivery forms of the pharmaceutical compositions containing one or more dosage units of the compounds of the invention may be prepared using suitable pharmaceutical excipients and compounding techniques now or later known or available to those skilled in the art. The compositions may be administered in the inventive methods by oral, parenteral, rectal, topical, or ocular routes, or by inhalation.

The preparation may be in the form of tablets, capsules, sachets, dragees, powders, granules, lozenges, powders for reconstitution, liquid preparations, or suppositories. Preferably, the compositions are formulated for intravenous infusion, topical administration, or oral administration.

For oral administration, the compounds of the invention can be provided in the form of tablets or capsules, or as a solution, emulsion, or suspension. To prepare the oral compositions, the compounds may be formulated to yield a dosage of, e.g., from about 0.01 to about 100 mg/kg daily, or from about 0.05 to about 35 mg/kg daily, or from about 0.1 to about 10 mg/kg daily.

Oral tablets may include a compound according to the invention mixed with pharmaceutically acceptable excipients such as inert diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are suitable disintegrating agents. Binding agents may include starch and gelatin. The lubricating agent, if present, may be magnesium stearate, stearic acid or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, compounds of the invention may be mixed with a solid, semi-solid, or liquid diluent. Soft gelatin capsules may be prepared by mixing the compound of the invention with water, an oil such as peanut oil or olive oil, liquid paraffin, a mixture of mono and diglycerides of short chain fatty acids, polyethylene glycol 400, or propylene glycol.

Liquids for oral administration may be in the form of suspensions, solutions, emulsions or syrups or may be presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The compounds of this invention may also be administered by non-oral routes. For example, the compositions may be formulated for rectal administration as a suppository. For parenteral use, including intravenous, intramuscular, intraperitoneal, or subcutaneous routes, the compounds of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms will be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses may range from about 1 to 1000 μg/kg/minute of compound, admixed with a pharmaceutical carrier over a period ranging from several minutes to several days.

For topical administration, the compounds may be mixed with a pharmaceutical carrier at a concentration of about 0.1% to about 10% of drug to vehicle. Another mode of administering the compounds of the invention may utilize a patch formulation to affect transdermal delivery.

Compounds of the invention may alternatively be administered in methods of this invention by inhalation, via the nasal or oral routes, e.g., in a spray formulation also containing a suitable carrier.

Exemplary compounds useful in methods of the invention will now be described by reference to the illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified, the variables are as defined above in reference to Formula (I). Reactions may be performed between the melting point and the reflux temperature of the solvent, and preferably between 0° C. and the reflux temperature of the solvent.

SCHEME A

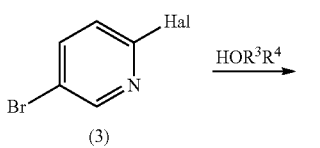

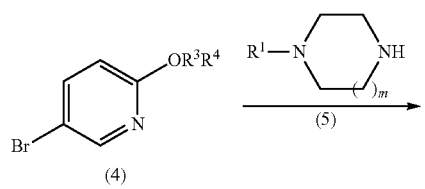

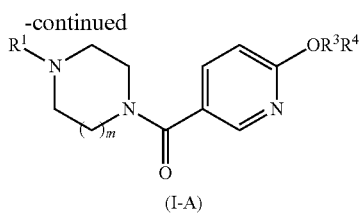

(I-A)

In some embodiments, compounds of Formula (I) are prepared as shown in Scheme A. 3-Bromo-pyridines (3), where Hal is bromo, chloro, or fluoro, are commercially available or prepared using methods known to one skilled in the art. Displacement of the Hal substituent is accomplished by reaction with reagents HOR$^3$R$^4$, in the presence of a suitable base such as NaOH, KOH, K$_2$CO$_3$, Na$_2$CO$_3$, Cs$_2$CO$_3$, NaH, or a mixture thereof, in a polar solvent such as N,N-dimethylformamide (DMF), ethylene glycol dimethyl ether (DME), N,N-dimethylacetamide (DMA), dimethylsulfoxide (DMSO), acetonitrile, or a mixture thereof, at a temperature between room temperature and the reflux temperature of the solvent, or subject to microwave irradiation, to provide ethers (4). Transition metal-catalyzed reaction of bromides (4) with amines (5) and a CO equivalent, such as CO gas or Mo(CO)$_6$, in the presence of a suitable palladium (II) catalyst, and optional additives such as t-Bu$_3$PHBF$_4^+$, at a temperature between room temperature and the reflux temperature of the solvent, or subject to microwave irradiation, provide compounds of Formula (I) where Y is N and R$^2$ is —OR$^3$R$^4$ (Formula I-A). Alternatively, halogen-metal exchange of the bromine atom of (4) by treatment with n-BuLi or t-BuLi and quenching with a CO$_2$ equivalent provides the corresponding carboxylic acids. Amide coupling of such acids with amines (5), in the presence of coupling agents known to one skilled in the art, also provides compounds of Formula (I-A). One skilled in the art will recognize that the R$^1$ substituent may be carried through the sequence as a suitable protecting group (such as a tert-butylcarbamoyl, or Boc, group), and installed at a later point in the sequence by, for example, reductive amination protocols.

dichloroethane (DCE), toluene, isopropyl acetate, or a mixture thereof, to form amides (7). Displacement of the Hal group as described in Scheme A provides compounds of Formula (I-A).

SCHEME C

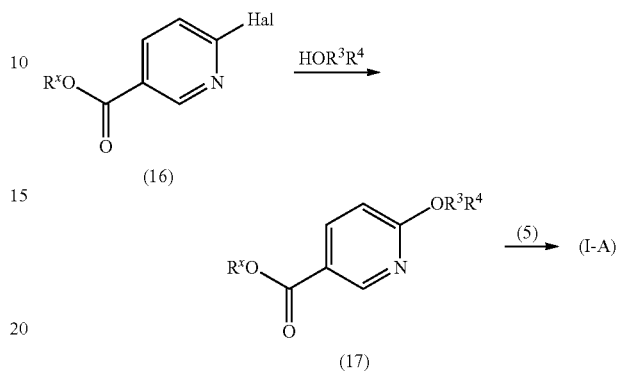

In further embodiments, compounds of Formula (I-A) are prepared from compounds (16), where R$^x$ is methyl or ethyl, and Hal is bromo, chloro, or fluoro, according to Scheme C. Displacement of the Hal substituent with a reagent HOR$^3$R$^4$, as described in Scheme A, gives a compound of formula (17). Reaction of a compound (17) with an amine (5), in the presence of an organometallic reagent, such as an alkyl Grignard reagent or alkyllithium reagent, in solvent such as tetrahydrofuran (THF), diethyl ether (Et$_2$O), methyl tert-butyl ether (MTBE), 2-methyl-THF, or a mixture thereof, at a temperature between about 0° C. and about 30° C., gives a compound of Formula (I-A). Examples of suitable organometallic reagents include R$^y$MgBr, R$^y$MgCl, or R$^y$Li, where R$^y$ is methyl, ethyl, propyl, isopropyl, butyl, or hexyl. Where a protecting group is used in place of R$^1$, such a protecting group may be removed through standard deprotection methods, and R$^1$ installed by reductive amination protocols.

SCHEME B

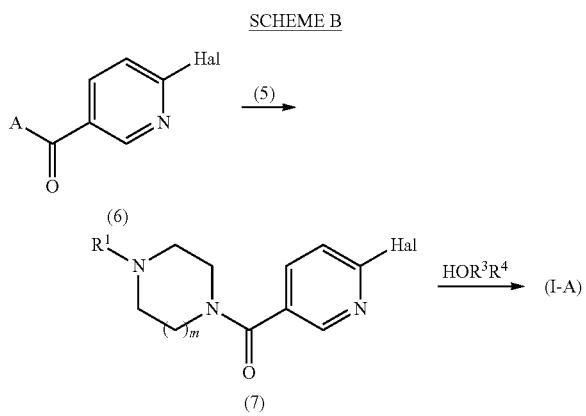

In other embodiments, compounds of Formula (I-A) are prepared as shown in Scheme B. Amide coupling of pyridine carboxylic acids (6) (where A is OH) with amines (5) provides amides (7). Alternatively, acid chlorides (6) (where A is Cl) may be reacted with amines (5) in the presence of a suitable base such as aq. NaOH, aq. KOH, Et$_3$N, iPr$_2$NEt, pyridine, or a mixture thereof, in a solvent such as CH$_2$Cl$_2$,

SCHEME D

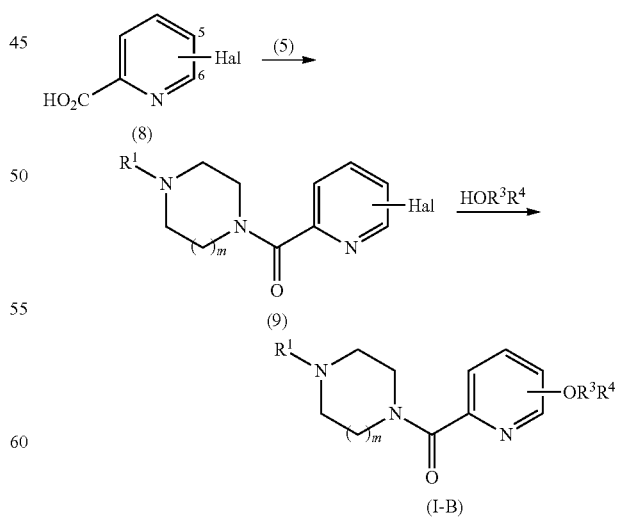

Referring to Scheme D, pyridines (8), where the Hal substituent is at the 5- or 6-position of the pyridine are coupled with amines (5) using general amide coupling methods to give amides (9). Replacement of the Hal substituent with —OR$^3$R$^4$ is accomplished by: 1) displacement by HOR$^3$R$^4$ reagents under basic conditions as described in Scheme A; or 2) Ullmann coupling in the presence of a suitable copper (I) catalyst, such as CuI, in a solvent such as DMF, DMSO, hexamethylphosphoramide (HMPA), or a mixture thereof. The displacement provides compounds of Formula (I) where Y is CR$^a$, R$^a$ is —OR$^3$R$^4$, and R$^2$ is —H or compounds of Formula (I) where Y is CH and R$^2$ is —OR$^3$R$^4$ (Formula I-B).

or regioisomers, by enantio-, diastero-, or regiospecific synthesis, or by resolution. Compounds prepared according to the schemes above may alternately be obtained as racemic (1:1) or non-racemic (not 1:1) mixtures or as mixtures of diastereomers or regioisomers. Where racemic and non-racemic mixtures of enantiomers are obtained, single enantiomers may be isolated using conventional separation methods known to one skilled in the art, such as chiral chromatography, recrystallization, diastereomeric salt formation, deriva-

SCHEME E

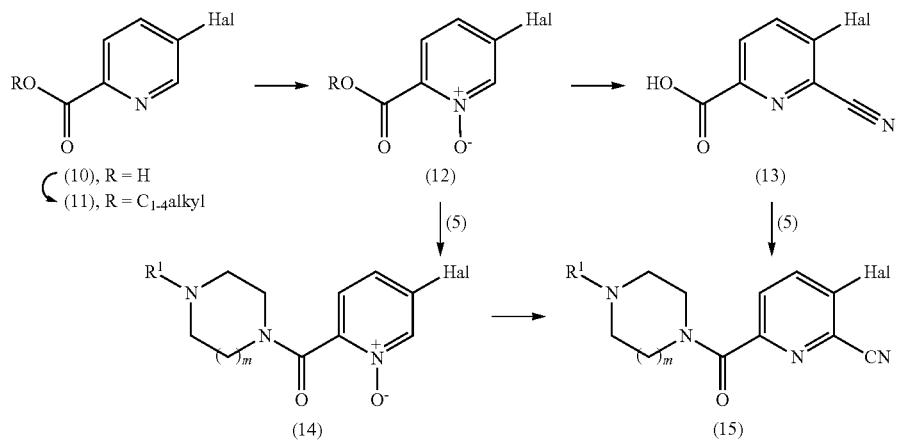

Compounds of Formula (I) where X is N, Y is CR$^a$, R$^a$ is —CN, and R$^2$ is —OR$^3$R$^4$ (Formula I-C, not shown) may be prepared from cyano amides (15), which are accessed as shown in Scheme E. Pyridine-2-carboxylic acids (10) are converted to the N-oxide analogs (12) by reaction with urea-hydrogen peroxide complex and trifluoroacetic acid anhydride. Installation of the cyano substituent is accomplished by reaction with trimethylsilyl cyanide (TMSCN) and dimethylcarbamyl chloride to provide nitrile acids (13). Alternatively, acids (10) may be esterified according to known methods to give esters (11), which may be converted to N-oxide esters (12). Following reaction with TMSCN and dimethylcarbamyl chloride to install the cyano group, hydrolysis of the ester group provides acids (13). Acids (13) are converted to cyano amides (15) by amide coupling with amines (5) as described in Scheme A. Alternatively, N-oxides (12), where R is —H, may be coupled with amines (5) directly, using amide coupling methods as described in Scheme A. N-Oxide amides (14) are reacted with TMSCN and dimethylcarbamyl chloride to give the corresponding cyano amides (15). Reaction of amides (15) via displacement or Ullmann coupling protocols as described in Schemes A and D provide compounds of Formula (I-C). Nitriles (15) are reduced to the corresponding aminomethyl analogs or hydrolyzed to form the corresponding acids or amides (not shown).

Those skilled in the art will recognize that several of the chemical transformations described above may be performed in a different order than that depicted in the above Schemes.

Compounds of Formula (I) may be converted to their corresponding salts using methods known to those skilled in the art. For example, amines of Formula (I) may be treated with trifluoroacetic acid (TFA), HCl, maleic acid, or citric acid in a solvent such as Et$_2$O, CH$_2$Cl$_2$, THF, or methanol (MeOH) to provide the corresponding salt forms.

Compounds prepared according to the schemes described above may be obtained as single enantiomers, diastereomers, tization into diastereomeric adducts, biotransformation, or enzymatic transformation. Where regioisomeric or diastereomeric mixtures are obtained, single isomers may be separated using conventional methods such as chromatography or crystallization.

The following examples are provided to further illustrate the invention and various preferred embodiments.

EXAMPLES

Chemistry

In preparing the compounds described in the examples below and obtaining the corresponding analytical data, the following experimental and analytical protocols were followed unless otherwise indicated.

Unless otherwise specified, reaction mixtures were magnetically stirred at room temperature (rt) under a N$_{2(g)}$ atmosphere. Where solutions were "dried," they were generally dried over a drying agent such as Na$_2$SO$_4$ or MgSO$_4$. Where mixtures, solutions, and extracts were "concentrated", they were typically concentrated on a rotary evaporator under reduced pressure.

Normal phase flash column chromatography (FCC) was typically performed with RediSep® silica gel columns using MeOH/DCM or 2 M NH$_3$ in MeOH/DCM as eluent, unless otherwise indicated.

Reverse phase high performance liquid chromatography (HPLC) was performed on a Gilson HPLC with an Xterra Prep RP$_{18}$ (5 μm, 30×100 mm) column, and a gradient of 10 to 99% acetonitrile/water (20 mM NH$_4$OH) over 12 min, and a flow rate of 30 mL/min.

Mass spectra (MS) were obtained on an Agilent series 1100 MSD using electrospray ionization (ESI) in positive mode unless otherwise indicated. Calculated (calcd.) mass corresponds to the exact mass.

Nuclear magnetic resonance (NMR) spectra were obtained on Bruker model DRX spectrometers. The format of the $^1$H NMR data below is: chemical shift in ppm downfield of the tetramethylsilane reference (multiplicity, coupling constant J in Hz, integration).

Chemical names were generated using ChemDraw Ultra 6.0.2 (CambridgeSoft Corp., Cambridge, Mass.).

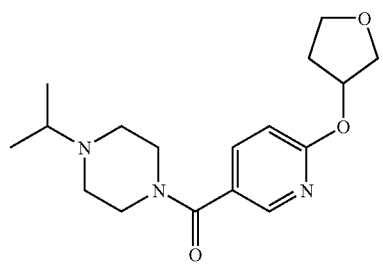 [SMILES: CC(C)N1CCN(C(=O)c2ccc(OC3CCOC3)nc2)CC1]

Example 1

(4-isopropyl-piperazin-1-yl)-[6-(tetrahydro-furan-3-yloxy)-pyridin-3-yl]-methanone hydrochloride salt Step A: 5-Bromo-2-(tetrahydro-furan-3-yloxy)-pyridine. To a solution of 5-bromo-2-fluoropyridine (1.5 mL, 14.2 mmol) in DMF (14 mL) was added $Cs_2CO_3$ (9.3 g, 28.5 mmol) and 3-hydroxytetrahydrofuran (1.7 mL, 21.3 mmol). The reaction mixture was heated at 90° C. for 3 days then allowed to cool to room temperature (rt). Water was added and product was filtered off, washed with water, and dried under vacuum overnight (3.5 g, 100%). MS (ESI): mass calcd. for $C_9H_{10}BrNO_2$, 243.0; m/z found, 244.3, 246.3 $[M+H]^+$. $^1$H NMR ($CDCl_3$): 8.17 (d, J=2.1 Hz, 1H), 7.64 (dd, J=8.8, 2.6 Hz, 1H), 6.66 (dd, J=8.7, 0.5 Hz, 1H) 5.52-5.48 (m, 1H), 4.04-3.95 (m, 2H), 3.93-3.86 (m, 2H), 2.30-2.19 (m, 1H), 2.15-2.08 (m, 1H).

Step B. To a vial charged with 5-bromo-2-(tetrahydro-furan-3-yloxy)-pyridine (0.293 g, 1.2 mmol), $Na_2CO_3$ (0.318 g, 3.0 mmol), isopropylpiperazine (0.143 mL, 1.0 mmol), trans-di-μ-acetatobis[2-(di-o-tolylphosphino)benzyl]di-palladium (II) (Hermann's catalyst; 47 mg, 0.05 mmol), and $Mo(CO)_6$ (132 mg, 0.5 mmol) was added 2 mL of pure water. The reaction mixture was heated in the microwave for 10 min at 170° C., cooled to rt and filtered through a pad of diatomaceous earth. The filtrate was diluted with saturated (satd.) aqueous (aq.) $NaHCO_3$ and extracted with $CH_2Cl_2$. The combined organic layers were dried ($Na_2SO_4$), filtered and concentrated. The residue was purified by FCC (2 M $NH_3$ in MeOH/$CH_2Cl_2$) to give the desired product (105 mg, 33%). MS (ESI): mass calcd. for $C_{17}H_{25}N_3O_3$, 319.2; m/z found, 320.5 $[M+H]^+$. $^1$H NMR ($CDCl_3$): 8.24 (dd, J=2.39, 0.6 Hz, 1H), 7.67 (dd, J=8.5, 2.4 Hz, 1H), 6.76 (dd, J=8.5, 0.6 Hz, 1H), 5.61-5.56 (m, 1H), 4.07-3.96 (m, 2H), 3.95-3.87 (m, 2H), 3.84-3.39 (m, 4H), 2.79-2.68 (m, 1H), 2.63-2.44 (m, 4H), 2.33-2.21 (m, 1H), 2.19-2.10 (m, 1H), 1.05 (d, J=6.5 Hz, 6H). The free base was dissolved in $CH_2Cl_2$ and treated with excess 1.25 M HCl in methanol. The solvent and excess HCl were removed under vacuum to provide the HCl salt for biological testing.

The compounds in Examples 2-9 were prepared using methods analogous to those described for Example 1. Yields and analytical data are provided for the free base forms.

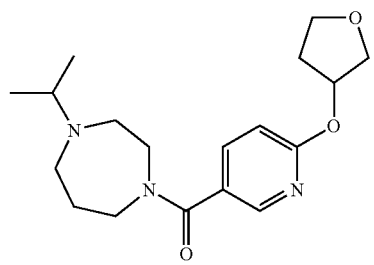 [SMILES: CC(C)N1CCCN(C(=O)c2ccc(OC3CCOC3)nc2)CC1]

Example 2

(4-Isopropyl-[1,4]diazepan-1-yl)-[6-(tetrahydro-furan-3-yloxy)-pyridin-3-yl]-methanone hydrochloride salt Yield: 135 mg, 40%. MS (ESI): mass calcd. for $C_{18}H_{27}N_3O_3$, 333.2; m/z found, 334.5 $[M+H]^+$. $^1$H NMR ($CDCl_3$): 8.18 (s, 1H), 7.61 (dd, J=8.5, 2.3 Hz, 1H), 6.71 (d, J=8.5 Hz, 1H), 5.56-5.51 (m, 1H), 3.99 (dd, J=10.4, 4.8 Hz, 1 H), 3.97-3.91 (m, 1H), 3.91-3.81 (m, 2H), 3.72-3.67 (m, 2H), 3.48-3.42 (m, 2H), 2.95-2.79 (m, 1H), 2.77-2.71 (m, 1H), 2.66-2.54 (m, 3H), 2.26-2.16 (m, 1H), 2.13-2.06 (m, 1H), 1.89-1.83 (m, 1H), 1.77-1.69 (m, 1H), 0.98 (d, J=6.4 Hz, 3H), 0.94 (d, J=6.9 Hz, 3H).

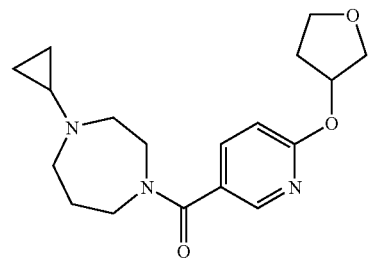 [SMILES: O=C(c1ccc(OC2CCOC2)nc1)N1CCCN(C2CC2)CC1]

Example 3

(4-Cyclopropyl-[1,4]diazepan-1-yl)-[6-(tetrahydro-furan-3-yloxy)-pyridin-3-yl]-methanone Yield: 22 mg, 6%. MS (ESI): mass calcd. for $C_{18}H_{25}N_3O_3$, 331.19; m/z found, 332.5 $[M+H]^+$. $^1$H NMR ($CDCl_3$): 8.22 (s, 1H), 7.65 (d, J=8.3 Hz, 1H), 6.75 (d, J=8.5 Hz, 1H), 5.60-5.56 (m, 1H), 4.04 (dd, J=10.4, 4.7 Hz, 1H), 4.02-3.97 (m, 1H), 3.95-3.86 (m, 2H), 3.77-3.71 (m, 2H), 3.56-3.48 (m, 2H), 2.99-2.92 (m, 1H), 2.88-2.77 (m, 3H), 2.31-2.21 (m, 1H), 2.18-2.11 (m, 1H), 1.97-1.77 (m, 3H), 0.53-0.34 (m, 4H).

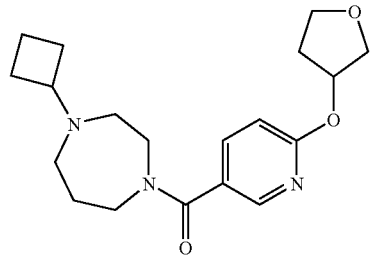 [SMILES: O=C(c1ccc(OC2CCOC2)nc1)N1CCCN(C2CCC2)CC1]

Example 4

(4-Cyclobutyl-[1,4]diazepan-1-yl)-[6-(tetrahydrofuran-3-yloxy)-pyridin-3-yl]-methanone Yield: 132 mg, 38%. MS (ESI): mass calcd. for $C_{19}H_{27}N_3O_3$, 345.2; m/z found, 346.6 [M+H]$^+$. $^1$H NMR (CDCl$_3$): 8.22 (s, 1H), 7.65 (dd, J=8.5, 2.4 Hz, 1H), 6.75 (dd, J=8.6, 0.6 Hz, 1H), 5.60-5.55 (m, 1H), 4.03 (dd, J=10.4, 4.7 Hz, 1H), 4.02-3.96 (m, 1H), 3.94-3.86 (m, 2H), 3.81-3.72 (m, 2H), 3.57-3.49 (m, 2H), 2.97-2.81 (m, 1H), 2.66-2.58 (m, 1H), 2.54-2.41 (m, 3H), 2.30-2.22 (m, 1H), 2.17-2.10 (m, 1H), 2.09-1.91 (m, 3H), 1.90-1.56 (m, 5H).

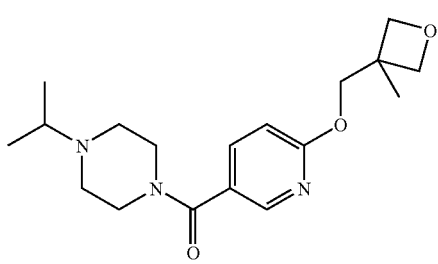 [SMILES: CC(C)N1CCN(C(=O)c2ccc(OCC3(C)COC3)nc2)CC1]

Example 5

(4-isopropyl-piperazin-1-yl)-[6-(3-methyl-oxetan-3-ylmethoxy)-pyridin-3-yl]-methanone hydrochloride salt Step A: 5-Bromo-2-(3-methyl-oxetan-3-ylmethoxy)-pyridine. Yield: 3.5 g, 95%. MS (ESI): mass calcd. for $C_{10}H_{12}NO_2$, 257.01; m/z found, 258.3, 260.3 [M+H]$^+$. $^1$H NMR (CDCl$_3$): 8.19 (dd, J=2.6, 0.6 Hz, 1H), 7.66 (dd, J=8.7, 2.6 Hz, 1H), 6.71 (dd, J=8.7, 0.6 Hz, 1H), 4.63 (d, J=5.9 Hz, 2H), 4.44 (d, J=5.9 Hz, 2H), 4.34 (s, 2H), 1.42 (s, 3H).

Step B. Yield: 11 mg, 3%. MS (ESI): mass calcd. for $C_{18}H_{27}N_3O_3$, 333.21; m/z found, 334.5 [M+H]$^+$. $^1$H NMR (CDCl$_3$): 8.25 (dd, J=2.4, 0.5 Hz, 1H), 7.70 (dd, J=8.5, 2.4 Hz, 1H), 6.82 (dd, J=8.5, 0.5 Hz, 1H), 4.64 (d, J=5.9 Hz, 2H), 4.45 (d, J=5.9 Hz, 2H), 4.41 (s, 2H), 3.87-3.42 (m, 4H), 2.77-2.71 (m, 1H), 2.66-2.42 (m, 4H), 1.43 (s, 3H), 1.05 (d, J=6.5 Hz, 6H).

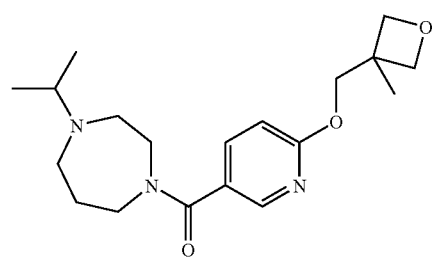 [SMILES: CC(C)N1CCCN(C(=O)c2ccc(OCC3(C)COC3)nc2)CC1]

Example 6

(4-Isopropyl-[1,4]diazepan-1-yl)-[6-(3-methyl-oxetan-3-ylmethoxy)-pyridin-3-yl]-methanone hydrochloride salt Yield: 11 mg, 3%. MS (ESI): mass calcd. for $C_{19}H_{29}N_3O_3$, 347.2; m/z found, 348.5 [M+H]$^+$. $^1$H NMR (CDCl$_3$): 8.24 (s, 1H), 7.69 (dd, J=8.5, 1.8 Hz, 1H), 6.81 (d, J=8.5 Hz, 1H), 4.65 (d, J=5.9 Hz, 2H), 4.45 (d, J=5.9 Hz, 2H), 4.40 (s, 2H), 3.81-3.71 (m, 2H), 3.54-3.48 (m, 2H), 3.03-2.77 (m, 2H), 2.74-2.60 (m, 3H), 1.96-1.87 (m, 1H), 1.72-1.62 (m, 1H), 1.43 (s, 3H), 1.08-0.97 (m, 6H).

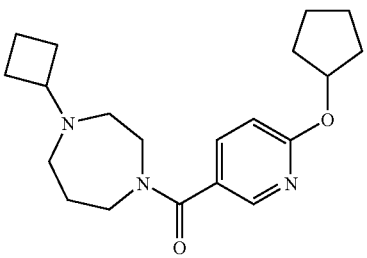 [SMILES: O=C(c1ccc(OC2CCCC2)nc1)N1CCCN(C2CCC2)CC1]

Example 7

(4-Cyclobutyl-[1,4]diazepan-1-yl)-(6-cyclopentyloxy-pyridin-3-yl)-methanone

Step A: 5-Bromo-2-cyclopentyloxy-pyridine. Yield: 1.69 g, 82%. MS (ESI): mass calcd. for $C_{10}H_{12}BrNO$, 241.01; m/z found, 242.3, 244.3 [M+H]$^+$. $^1$H NMR (CDCl$_3$): 8.18 (d, J=2.5 Hz, 1H), 7.60 (dd, J=8.8, 2.6 Hz, 1H), 6.59 (d, J=8.8 Hz, 1H), 5.34-5.30 (m, 1H), 1.99-1.90 (m, 2H), 1.82-1.73 (m, 4H), 1.67-1.58 (m, 2H).

Step B. Yield: 114 mg, 33%. MS (ESI): mass calcd. for $C_{20}H_{29}N_3O_2$, 343.2; m/z found, 344.6 [M+H]$^+$. $^1$H NMR (CDCl$_3$): 8.21 (s, 1H), 7.60 (dd, J=8.5, 2.4 Hz, 1H), 6.65 (dd, J=8.5, 0.5 Hz, 1H), 5.40-5.35 (m, 1H), 3.77-3.67 (m, 2H), 3.56-3.47 (m, 2H), 2.91-2.77 (m, 1H), 2.62-2.55 (m, 1H), 2.51-2.36 (m, 3H), 2.06-1.87 (m, 5H), 1.86-1.70 (m, 7H), 1.69-1.53 (m, 4H).

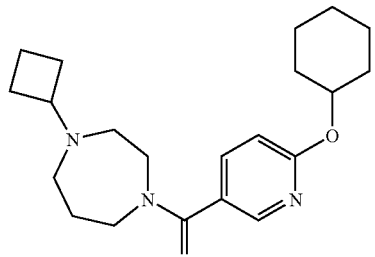

Example 8

(4-Cyclobutyl-[1,4]diazepan-1-yl)-(6-cyclohexyloxy-pyridin-3-yl)-methanone

Step A: 5-Bromo-2-cyclohexyloxy-pyridine. Yield: 1.73 g, 79%. MS (ESI): mass calcd. for $C_{10}H_{14}BrNO$, 255.03; m/z found, 256.4, 258.4 [M+H]$^+$. $^1$H NMR (CDCl$_3$): 8.15 (d, J=2.5 Hz, 1H), 7.60 (dd, J=8.8, 2.6 Hz, 1H), 6.60 (d, J=8.8 Hz, 1H), 4.99-4.93 (m, 1H), 2.02-1.94 (m, 2H), 1.82-1.75 (m, 2H), 1.62-1.54 (m, 1H), 1.54-1.36 (m, 4H), 1.34-1.24 (m, 1H).

Step B. Yield: 100 mg, 28%. MS (ESI): mass calcd. for $C_{21}H_{31}N_3O_2$, 357.2; m/z found, 358.5 [M+H]$^+$. $^1$H NMR (CDCl$_3$): 8.19 (s, 1H), 7.61 (dd, J=8.5, 2.4 Hz, 1H), 6.67 (dd, J=8.5, 0.6 Hz, 1H), 5.06-4.99 (m, 1H), 3.77-3.69 (m, 2 H), 3.57-3.47 (m, 2H), 2.92-2.78 (m, 1H), 2.63-2.56 (m, 1H), 2.51-2.38 (m, 3H), 2.07-1.89 (m, 5H), 1.87-1.71 (m, 5H), 1.70-1.35 (m, 7H), 1.32-1.22 (m, 1H).

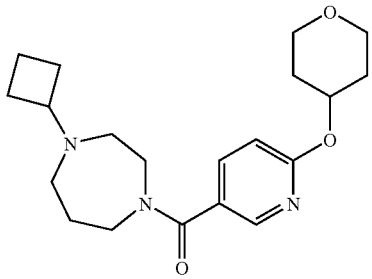 [SMILES: O=C(c1ccc(OC2CCOCC2)nc1)N1CCCN(C2CCC2)CC1]

Example 9

(4-Cyclobutyl-[1,4]diazepan-1-yl)-[6-(tetrahydro-pyran-4-yloxy)-pyridin-3-yl]-methanone Step A: 5-Bromo-2-(tetrahydro-pyran-4-yloxy)-pyridine. Yield: 2.16 g, 98%. MS (ESI): mass calcd. for $C_{10}H_{12}BrNO_2$, 257.01; m/z found, 258.1, 260.1 [M+H]$^+$. $^1$H NMR (CDCl$_3$): 8.15 (d, J=2.5 Hz, 1H), 7.63 (dd, J=8.8, 2.5 Hz, 1H), 6.64 (d, J=8.8 Hz, 1H), 5.20-5.14 (m, 1H), 4.01-3.93 (m, 2H), 3.60 (ddd, J=11.9, 9.2, 3.0 Hz, 2H), 2.08-2.01 (m, 2H), 1.81-1.72 (m, 2H).

Step B. Yield: 81 mg, 22%. MS (ESI): mass calcd. for $C_{20}H_{29}N_3O_3$, 359.22; m/z found, 360.6 [M+H]$^+$. $^1$H NMR (CDCl$_3$): 8.21 (s, 1H), 7.65 (dd, J=8.5, 2.4 Hz, 1H), 6.73 (dd, J=8.5, 0.6 Hz, 1H), 5.31-5.21 (m, 1H), 4.02-3.94 (m, 2H), 3.78-3.72 (m, 2H), 3.61 (ddd, J=11.9, 9.1, 2.9 Hz, 2H), 3.57-3.49 (m, 2H), 2.96-2.80 (m, 1H), 2.66-2.58 (m, 1H), 2.54-2.40 (m, 3H), 2.11-1.91 (m, 5), 1.90-1.73 (m, 5H), 1.67-1.50 (m, 2H).

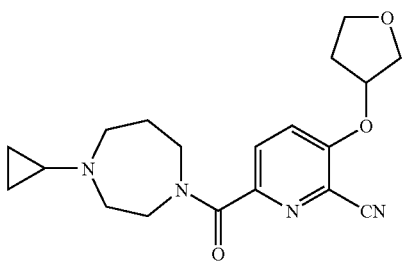 [SMILES: N#Cc1nc(C(=O)N2CCCN(C3CC3)CC2)ccc1OC1CCOC1]

Example 10

6-(4-Cyclopropyl-[1,4]diazepane-1-carbonyl)-3-(tetrahydro-furan-3-yloxy)-pyridine-2-carbonitrile Step A: 5-Bromo-1-oxo-pyridine-2-carboxylic acid. To a 0° C. mixture of 5-bromo-picolinic acid (18.5 g, 91.6 mmol) and urea hydrogen peroxide complex (18.2 g, 0.194 mol) in acetonitrile (275 mL) was added trifluoroacetic anhydride (26 mL, 0.187 mol). After 4.5 h, the mixture was treated with aq. Na$_2$S$_2$O$_3$ at 0° C., stirred for 10 min, and then extracted with CH$_2$Cl$_2$ (300 mL×5). The combined organic layers were concentrated to give the crude product, which was suspended in boiling water (500 mL) and filtered. The filtered solid was triturated with boiling MeOH (500 mL) twice, leaving a yellow solid. The aqueous and methanolic extracts were combined and concentrated to dryness to give >100% of the acid as a tan solid. MS (ESI): mass calcd. for $C_6H_4BrNO_3$, 216.94; m/z found, 218.1 [M+H]$^+$. $^1$H NMR (d$^6$-DMSO): 17.70 (s, 1H), 9.19 (d, J=1.5 Hz, 1H), 8.18-8.12 (m, 2H).

Step B: (5-Bromo-1-oxo-pyridin-2-yl)-(4-cyclopropyl-[1,4]diazepan-1-yl)-methanone. A mixture of 5-bromo-1-oxo-pyridine-2-carboxylic acid (10.0 g 45.9 mmol), 1-hydroxy-benzotriazole (HOBt; 9.93 g, 73.4 mmol), and 1-(3-dimethylaminopropyl)-3-ethylcarbodiimide (EDC; 13.4 g, 70.3 mmol) in DMF (300 mL) was stirred for 5 min and then treated with 1-cyclopropyl-[1,4]diazepane dihydrochloride (12.4 g, 58.4 mmol) and 1,8-diazabicyclo[5.4.0]undec-7-ene (DBU; 21.0 mL, 0.140 mol). After 22 h, the mixture was diluted with CH$_2$Cl$_2$ and washed with 1 N NaOH and water. The organic layer was dried and concentrated. The residue was purified by FCC to give the title compound (13.2 g, 85%). MS (ESI): mass calcd. for $C_{14}H_{18}BrN_3O_2$, 339.06; m/z found, 340.2 [M+H]$^+$.

Step C: 3-Bromo-6-(4-cyclopropyl-[1,4]diazepane-1-carbonyl)-pyridine-2-carbonitrile. A mixture of (5-bromo-1-oxo-pyridin-2-yl)-(4-cyclopropyl-[1,4]diazepan-1-yl)-methanone (13.1 g, 38.8 mmol), TMSCN (26.0 mL, 195 mmol), and dimethylcarbamyl chloride (18.0 mL, 195 mmol) was heated at 50° C. for 16 h. The mixture was allowed to cool to rt and was poured over ice water containing NaOH. The mixture was extracted with CH$_2$Cl$_2$ (2×), and the combined organic layers were dried and concentrated to give the crude product. The crude material was purified by FCC to give the title compound (13.6 g, 76%). MS (ESI): mass calcd. for $C_{15}H_{17}BrN_4O$, 348.06; m/z found, 349.6 [M+H]$^+$. $^1$H NMR (d$^6$-acetone): 8.42 (d, J=8.4 Hz, 1H), 7.83-7.81 (m, 1H), 3.70-3.68 (m, 2H), 3.55-3.52 (m, 2H), 2.93-2.91 (m, 1H), 2.87-2.80 (m, 3H), 1.96-1.87 (m, 2H), 1.84-1.80 (m, 1H), 0.46-0.44 (m, 1H), 0.43-0.41 (m, 1H), 0.37-0.35 (m, 1H), 0.32-0.30 (m, 1H).

Step D. A mixture of 3-bromo-6-(4-cyclopropyl-[1,4]diaz-epane-1-carbonyl)-pyridine-2-carbonitrile (0.600 g, 1.71 mmol), 3-hydroxytetrahydrofuran (301 mg, 3.41 mmol), and anhydrous Cs$_2$CO$_3$ (1.67 g, 5.13 mmol) in DMSO (7 mL) was heated by microwave irradiation at 150° C. for 35 min. The mixture was diluted with water and extracted with Et$_2$O. The combined organic layers were dried (Na$_2$CO$_3$) and concentrated. The residue was purified by FCC to give the title compound (280 mg, 46%). MS (ESI): mass calcd. for $C_{19}H_{24}N_4O_3$, 356.4; m/z found, 357.5 [M+H]$^+$. $^1$H NMR (CDCl$_3$): 7.94 (d, J=8.8 Hz, 1H), 7.35 (d, J=8.9 Hz, 1H), 5.08-5.04 (m, 1H), 4.12-3.93 (m, 4H), 3.77-3.72 (m, 2H), 3.69-3.63 (m, 2H), 2.98-2.92 (m, 2H), 2.87-2.81 (m, 2H), 2.35-2.25 (m, 1H), 2.25-2.18 (m, 1H), 1.97-1.83 (m, 3H), 0.51-0.35 (m, 4H).

The compounds in Examples 11-12 were prepared using methods analogous to those described for Example 10.

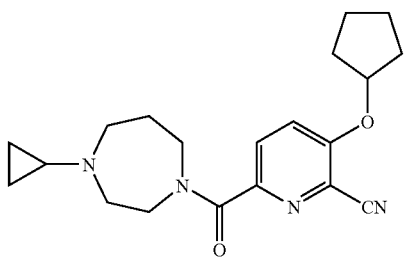 [SMILES: N#Cc1nc(C(=O)N2CCCN(C3CC3)CC2)ccc1OC1CCCC1]

Example 11

3-Cyclopentyloxy-6-(4-cyclopropyl-[1,4]diazepane-1-carbonyl)-pyridine-2-carbonitrile Yield: 33 mg, 5%. MS (ESI): mass calcd. for $C_{20}H_{26}N_4O_2$, 354.4; m/z found, 355.5 [M+H]$^+$. $^1$H NMR (CDCl$_3$): 7.92 (d, J=8.9 Hz, 1H), 7.40 (d, J=8.9 Hz, 1H), 4.93-4.88 (m, 1H), 3.78-3.73 (m, 2H), 3.71-3.65 (m, 2H), 2.98-2.92 (m, 2H), 2.87-2.81 (m, 2H), 1.99-1.84 (m, 9H), 1.75-1.65 (m, 2H), 0.51-0.36 (m, 4).

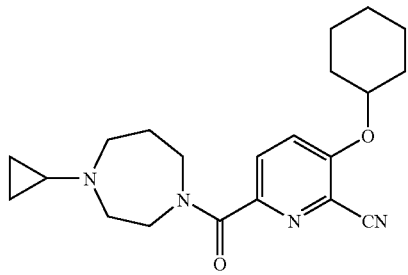 [SMILES: N#Cc1nc(C(=O)N2CCCN(C3CC3)CC2)ccc1OC1CCCCC1]

Example 12

3-Cyclohexyloxy-6-(4-cyclopropyl-[1,4]diazepane-1-carbonyl)-pyridine-2-carbonitrile Yield: 98 mg, 15%. MS (ESI): mass calcd. for $C_{21}H_{28}N_4O_2$, 368.4; m/z found, 369.6 [M+H]$^+$. $^1$H NMR (CDCl$_3$): 7.88 (d, J=8.9 Hz, 1H), 7.39 (d, J=9.0 Hz, 1H), 4.49-4.43 (m, 1H), 3.75-3.70 (m, 2H), 3.69-3.62 (m, 2H), 2.96-2.90 (m, 2H), 2.85-2.79 (m, 2H), 1.97-1.78 (m, 7H), 1.74-1.64 (m, 2H), 1.59-1.50 (m, 1H), 1.46-1.35 (m, 3H), 0.49-0.33 (m, 4H).

The compounds in Examples 13-39 may be prepared using methods analogous to those described in the preceding examples.

Example 13

(4-Isopropyl-[1,4]diazepan-1-yl)-[6-(tetrahydro-pyran-4-yloxy)-pyridin-3-yl]-methanone

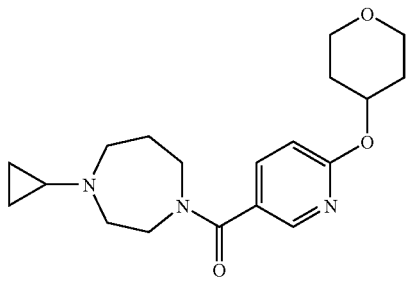 [SMILES: O=C(c1ccc(OC2CCOCC2)nc1)N1CCCN(C2CC2)CC1]

Example 14

(4-Cyclopropyl-[1,4]diazepan-1-yl)-[6-(tetrahydro-pyran-4-yloxy)-pyridin-3-yl]-methanone

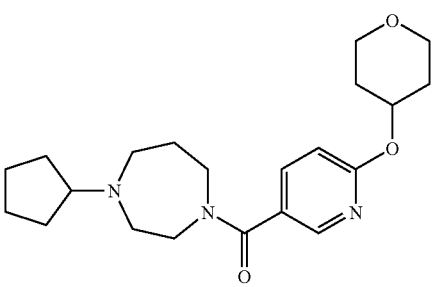 [SMILES: O=C(c1ccc(OC2CCOCC2)nc1)N1CCCN(C2CCCC2)CC1]

Example 15

(4-Cyclopentyl-[1,4]diazepan-1-yl)-[6-(tetrahydro-pyran-4-yloxy)-pyridin-3-yl]-methanone

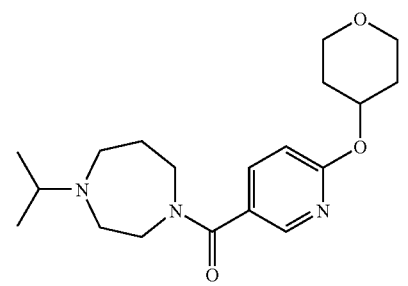

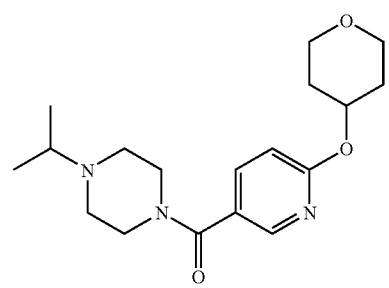 [SMILES: CC(C)N1CCN(C(=O)c2ccc(OC3CCOCC3)nc2)CC1]

Example 16

(4-Isopropyl-piperazin-1-yl)-[6-(tetrahydro-pyran-4-yloxy)-pyridin-3-yl]-methanone

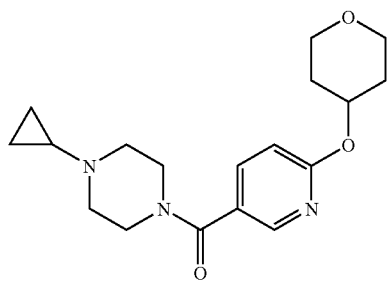 [SMILES: O=C(c1ccc(OC2CCOCC2)nc1)N1CCN(C2CC2)CC1]

Example 17

(4-Cyclopropyl-piperazin-1-yl)-[6-(tetrahydro-pyran-4-yloxy)-pyridin-3-yl]-methanone

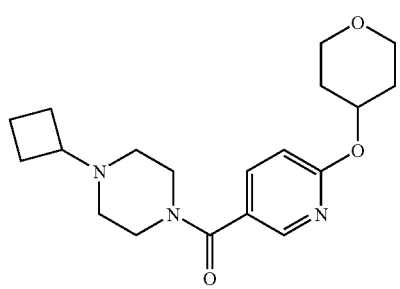 [SMILES: O=C(c1ccc(OC2CCOCC2)nc1)N1CCN(C2CCC2)CC1]

Example 18

(4-Cyclobutyl-piperazin-1-yl)-[6-(tetrahydro-pyran-4-yloxy)-pyridin-3-yl]-methanone

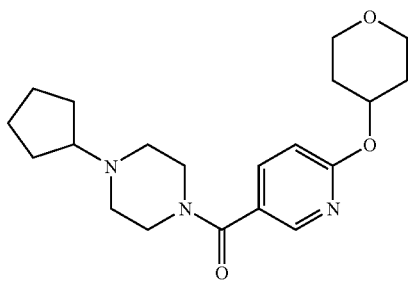 [SMILES: O=C(c1ccc(OC2CCOCC2)nc1)N1CCN(C2CCCC2)CC1]

Example 19

(4-Cyclopentyl-piperazin-1-yl)-[6-(tetrahydro-pyran-4-yloxy)-pyridin-3-yl]-methanone

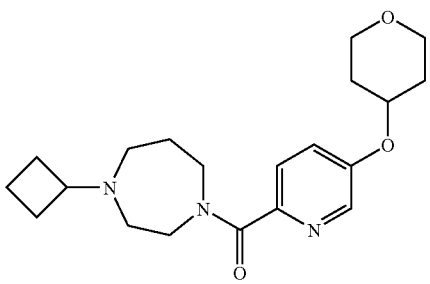 [SMILES: O=C(c1ccc(OC2CCOCC2)cn1)N1CCCN(C2CCC2)CC1]

Example 20

(4-Cyclobutyl-[1,4]diazepan-1-yl)-[5-(tetrahydro-pyran-4-yloxy)-pyridin-2-yl]-methanone

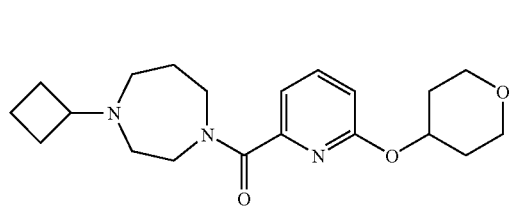 [SMILES: O=C(c1cccc(OC2CCOCC2)n1)N1CCCN(C2CCC2)CC1]

Example 21

(4-Cyclobutyl-[1,4]diazepan-1-yl)-[6-(tetrahydro-pyran-4-yloxy)-pyridin-2-yl]-methanone

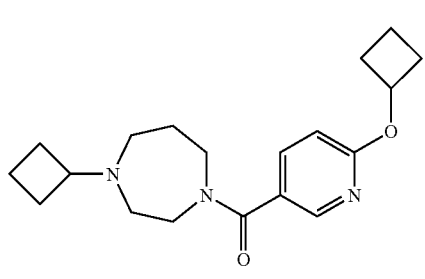 [SMILES: O=C(c1ccc(OC2CCC2)nc1)N1CCCN(C2CCC2)CC1]

Example 22

(6-Cyclobutoxy-pyridin-3-yl)-(4-cyclobutyl-[1,4]diazepan-1-yl)-methanone

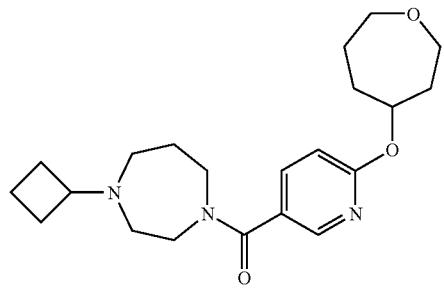 [SMILES: O=C(c1ccc(OC2CCCOCC2)nc1)N1CCCN(C2CCC2)CC1]

Example 23

(4-Cyclobutyl-[1,4]diazepan-1-yl)-[6-(oxepan-4-yloxy)-pyridin-3-yl]-methanone

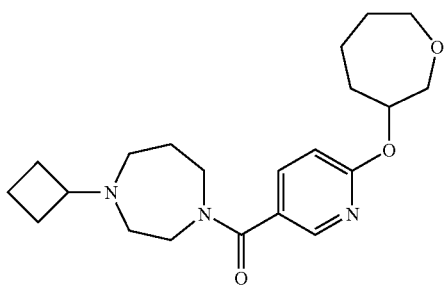 [SMILES: O=C(c1ccc(OC2CCCCOC2)nc1)N1CCCN(C2CCC2)CC1]

Example 24

(4-Cyclobutyl-[1,4]diazepan-1-yl)-[6-(oxepan-3-yloxy)-pyridin-3-yl]-methanone

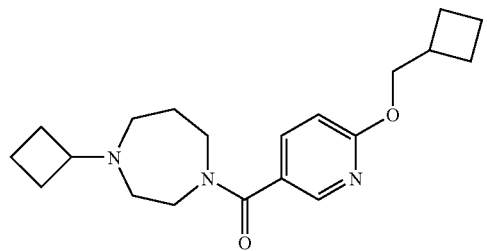 [SMILES: O=C(c1ccc(OCC2CCC2)nc1)N1CCCN(C2CCC2)CC1]

Example 25

(4-Cyclobutyl-[1,4]diazepan-1-yl)-(6-cyclobutyl-methoxy-pyridin-3-yl)-methanone

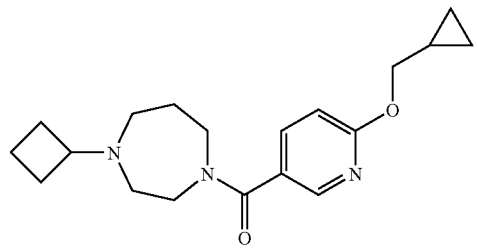 [SMILES: O=C(c1ccc(OCC2CC2)nc1)N1CCCN(C2CCC2)CC1]

Example 26

(4-Cyclobutyl-[1,4]diazepan-1-yl)-(6-cyclopropyl-methoxy-pyridin-3-yl)-methanone

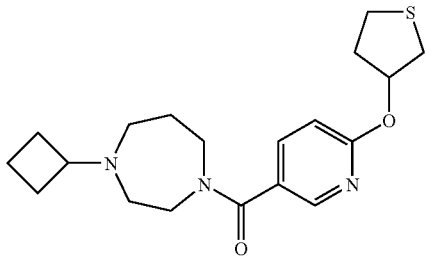 [SMILES: O=C(c1ccc(OC2CCSC2)nc1)N1CCCN(C2CCC2)CC1]

Example 27

(4-Cyclobutyl-[1,4]diazepan-1-yl)-[6-(tetrahydro-thiophen-3-yloxy)-pyridin-3-yl]-methanone

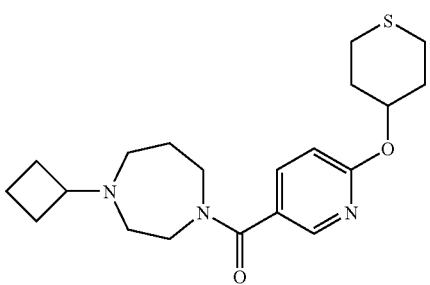 [SMILES: O=C(c1ccc(OC2CCSCC2)nc1)N1CCCN(C2CCC2)CC1]

Example 28

(4-Cyclobutyl-[1,4]diazepan-1-yl)-[6-(tetrahydro-thiopyran-4-yloxy)-pyridin-3-yl]-methanone

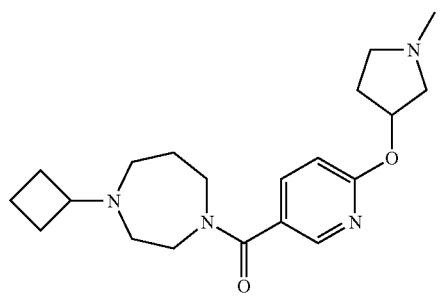 [SMILES: CN1CCC(Oc2ccc(C(=O)N3CCCN(C4CCC4)CC3)cn2)C1]

Example 29

(4-Cyclobutyl-[1,4]diazepan-1-yl)-[6-(1-methyl-pyrrolidin-3-yloxy)-pyridin-3-yl]-methanone

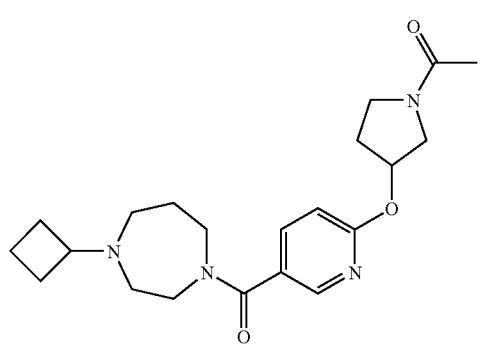 [SMILES: CC(=O)N1CCC(Oc2ccc(C(=O)N3CCCN(C4CCC4)CC3)cn2)C1]

Example 30

1-{3-[5-(4-Cyclobutyl-[1,4]diazepane-1-carbonyl)-pyridin-2-yloxy]-pyrrolidin-1-yl}-ethanone

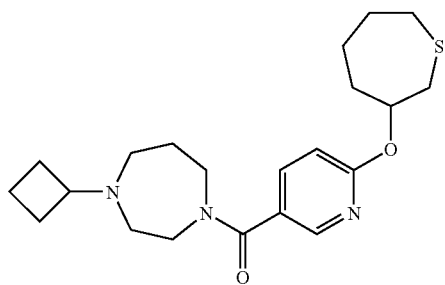 [SMILES: O=C(c1ccc(OC2CCCCSC2)nc1)N1CCCN(C2CCC2)CC1]

Example 31

(4-Cyclobutyl-[1,4]diazepan-1-yl)-[6-(thiepan-3-yloxy)-pyridin-3-yl]-methanone

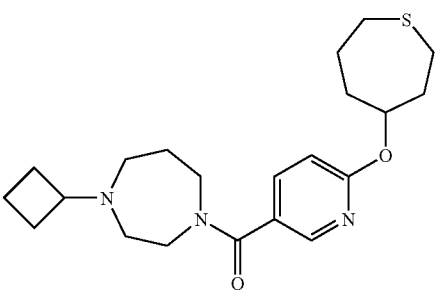

Example 32

(4-Cyclobutyl-[1,4]diazepan-1-yl)-[6-(thiepan-4-yloxy)-pyridin-3-yl]-methanone

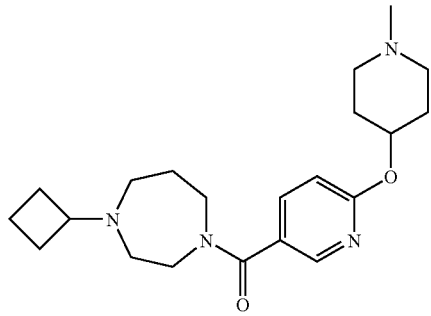 [SMILES: CN1CCC(Oc2ccc(C(=O)N3CCCN(C4CCC4)CC3)cn2)CC1]

Example 33

(4-Cyclobutyl-[1,4]diazepan-1-yl)-[6-(1-methyl-piperidin-4-yloxy)-pyridin-3-yl]-methanone

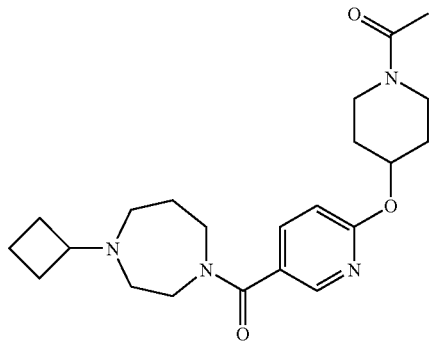 [SMILES: CC(=O)N1CCC(Oc2ccc(C(=O)N3CCCN(C4CCC4)CC3)cn2)CC1]

Example 34

1-{4-[5-(4-Cyclobutyl-[1,4]diazepane-1-carbonyl)-pyridin-2-yloxy]-piperidin-1-yl}-ethanone

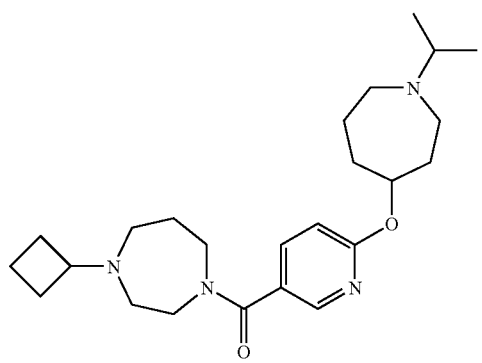 [SMILES: CC(C)N1CCCC(Oc2ccc(C(=O)N3CCCN(C4CCC4)CC3)cn2)CC1]

Example 35

(4-Cyclobutyl-[1,4]diazepan-1-yl)-[6-(1-isopropyl-azepan-4-yloxy)-pyridin-3-yl]-methanone

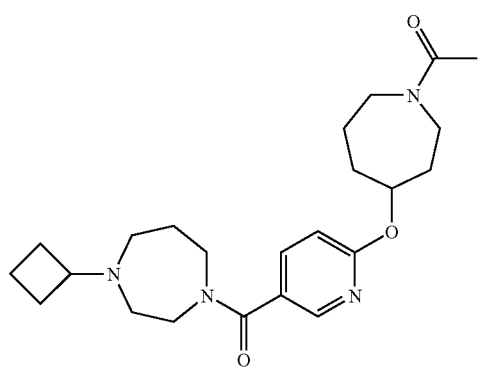 [SMILES: CC(=O)N1CCCC(Oc2ccc(C(=O)N3CCCN(C4CCC4)CC3)cn2)CC1]

Example 36

1-{4-[5-(4-Cyclobutyl-[1,4]diazepane-1-carbonyl)-pyridin-2-yloxy]-azepan-1-yl}-ethanone

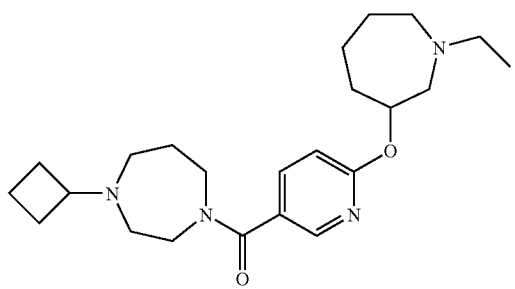 [SMILES: CCN1CCCCC(Oc2ccc(C(=O)N3CCCN(C4CCC4)CC3)cn2)C1]

Example 37

(4-Cyclobutyl-[1,4]diazepan-1-yl)-[6-(1-ethyl-azepan-3-yloxy)-pyridin-3-yl]-methanone

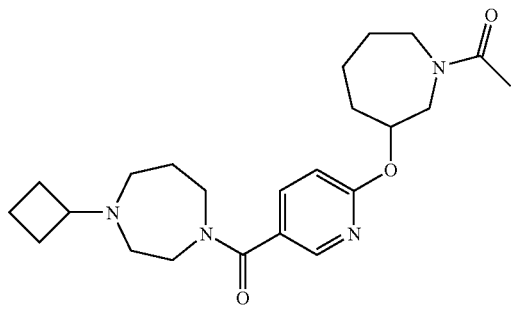 [SMILES: CC(=O)N1CCCCC(Oc2ccc(C(=O)N3CCCN(C4CCC4)CC3)cn2)C1]

Example 38

1-{3-[5-(4-Cyclobutyl-[1,4]diazepane-1-carbonyl)-pyridin-2-yloxy]-azepan-1-yl}-ethanone

Example 39

(4-Cyclopropyl-piperazin-1-yl)-[6-(tetrahydro-pyran-3-yloxy)-pyridin-3-yl]-methanone

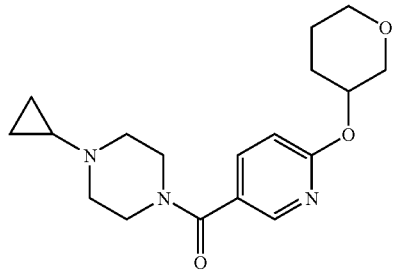 [SMILES: O=C(c1ccc(OC2CCCOC2)nc1)N1CCN(C2CC2)CC1]

Example 40

(4-Cyclobutyl-[1,4]diazepan-1-yl)-[6-(tetrahydro-pyran-4-yloxy)-pyridin-3-yl]-methanone.HCl

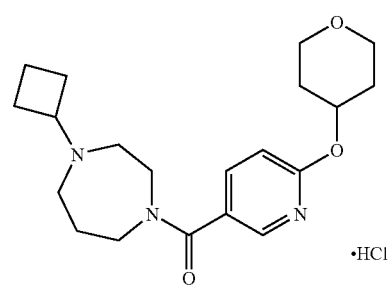 [SMILES: O=C(c1ccc(OC2CCOCC2)nc1)N1CCCN(C2CCC2)CC1 ; Cl]

To a solution of (4-cyclobutyl-[1,4]diazepan-1-yl)-[6-(tetrahydro-pyran-4-yloxy)-pyridin-3-yl]-methanone (6.17 g, 17.2 mmol) in IPA (100 mL) was added anhydrous HCl (5-6 M solution in IPA, 3.44 mL, 17.2 mmol). The mixture was then warmed to 80° C. and cooled to 60° C. to promote precipitation. Seed crystals were added at this point. Cooling to room temperature, filtering, washing with IPA (50 mL), and drying at 50° C. provided the title compound as a white crystalline solid (5.29 g, 78% yield). $^1$H-NMR: (400 MHz, DMSO) δ, 11.46 (bs, 1H), 8.29 (bs, 1H), 7.82 (bd, J=7.6 Hz, 1H), 6.86 (d, J=8.8 Hz, 1H), 5.22 (m, 1H), 4.18-3.22 (m, 11H), 3.10-2.90 (m, 2H), 2.48-2.25 (m, 3H), 2.25-1.97 (m, 5H), 1.78-1.59 (m, 4H). Anal. Calcd for $C_{20}H_{30}ClN_3O_3$: C, 60.67; H, 7.64; N, 10.61; Cl, 8.95. found C, 60.71; H, 7.90; N, 10.50; Cl, 8.88.

Biological Methods:

$H_3$ Receptor Binding (Human)

Binding of compounds to the cloned human $H_3$ receptors, stably expressed in SK-N-MC cells, was performed as described by Barbier, A. J. et al. (Br. J. Pharmacol. 2004, 143(5), 649-661).

$H_3$ Receptor Binding (Rat)

A rat brain without cerebellum (Zivic Laboratories Inc., Pittsburgh, Pa.) was homogenized in 50 mM Tris-HCl/5 mM EDTA and centrifuged at 1,000 rpm for 5 min. The supernatant was removed and recentrifuged at 15,000 rpm for 30 min. Pellets were rehomogenized in 50 mM Tris/5 mM EDTA (pH 7.4). Membranes were incubated with 0.8 nM N—[$^3$H]-α-methylhistamine plus/minus test compounds for 60 min at 25° C. and harvested by rapid filtration over GF/C glass fiber filters (pretreated with 0.3% polyethylenimine) followed by four washes with buffer. Nonspecific binding was defined in the presence of 100 μM histamine. Inhibitory concentration (responsible for 50% inhibition of maximal effect, $IC_{50}$) values were determined by a single site curve-fitting program (GraphPad, San Diego, Calif.) and converted to $K_i$ values based on a N—[$^3$H]-α-methylhistamine dissociation constant ($K_d$) of 0.8 nM.

Cyclic AMP Accumulation

Sublines of SK-N-MC cells were created that expressed a reporter construct and either the human or rat $H_3$ receptor. The $pA_2$ values were obtained as described by Barbier et al. (2004).

Data for compounds tested in the above assays are presented in Table 1 as an average of the results obtained (NT=not tested).

TABLE 1

| Ex. | Human $H_3 K_i$ (nM) | Rat $H_3 K_i$ (nM) | Human $pA_2$ | Rat $pA_2$ |
|---|---|---|---|---|
| 1 | 104 | NT | NT | NT |
| 2 | 9.0 | NT | NT | NT |
| 3 | 6.8 | NT | NT | NT |
| 4 | 1.3 | 58 | 9.48 | 7.84 |
| 5 | 5010 | NT | NT | NT |
| 6 | 37 | NT | NT | NT |
| 7 | 1.1 | 44 | 9.31 | 8.32 |
| 8 | 0.8 | 17 | 8.98 | 8.01 |
| 9 | 0.9 | 28* | 9.63 | 8.36 |
| 10 | 21 | NT | NT | NT |
| 11 | 6.0 | NT | NT | NT |
| 12 | 2.2 | NT | NT | NT |

*Compound tested as the trifluoroacetic acid salt.

What is claimed is:

1. A compound of Formula (I):

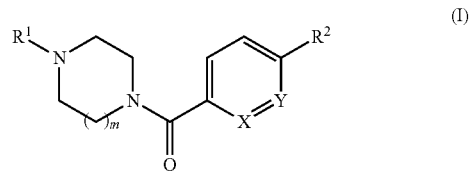

wherein $R^1$ is —$C_{1-5}$alkyl or a saturated cycloalkyl group;

m is 1 or 2;

$R^2$ is —H or —OCHR$^3$R$^4$;

where $R^3$ is —H; and $R^4$ is a cycloalkyl or heterocycloalkyl ring, unsubstituted or substituted with —$C_{1-4}$alkyl or acetyl;

or, $R^3$ and $R^4$ taken together with the carbon to which they are attached form a cycloalkyl or heterocycloalkyl ring, unsubstituted or substituted with —$C_{1-4}$ alkyl or acetyl;

X is N or CH; and

Y is N or CR$^a$;

where $R^a$ is —H, —OCHR$^3$R$^4$, —CH$_2$NR$^b$R$^c$, —CN, —CO$_2$C$_{1-4}$alkyl, —CO$_2$H, or —CONR$^b$R$^c$;

$R^b$ and $R^c$ are each independently —H or —$C_{1-4}$alkyl;

with the proviso that one of X and Y is N and one of $R^2$ and $R^a$ is —OCHR$^3$R$^4$;

or a pharmaceutically acceptable salt.

2. A compound as defined in claim 1, wherein $R^1$ is isopropyl, cyclopropyl, cyclobutyl, or cyclopentyl.

3. A compound as defined in claim 1, wherein m is 2.

4. A compound as defined in claim 1, wherein X is N.

5. A compound as defined in claim 1, wherein Y is N.

6. A compound as defined in claim 1, wherein $R^2$ is —H and $R^a$ is —OCHR$^3$R$^4$.

7. A compound as defined in claim 1, wherein $R^2$ is —OCHR$^3$R$^4$ and $R^a$ is not —OCHR$^3$R$^4$.

8. A compound as defined in claim 1, wherein $R^3$ is —H and $R^4$ is cyclopropyl, cyclocyclobutyl, or 3-methyl-oxetan-3-yl.

9. A compound as defined in claim 1, wherein $R^3$ and $R^4$ taken together with the carbon to which they are attached form cyclobutyl, cyclopentyl, cyclohexyl, tetrahydrofuranyl, tetrahydropyranyl, oxepanyl, tetrahydrothiophenyl, tetrahydrothiopyranyl, pyrrolidinyl, thiepanyl, piperidinyl, or azepanyl, unsubstituted or substituted with methyl, ethyl, isopropyl, or acetyl.

10. A compound as defined in claim 1, wherein —OCHR$^3$R$^4$ is tetrahydro-furan-3-yloxy, 3-methyl-oxetan-3-ylmethoxy, cyclopentyloxy, cyclohexyloxy, tetrahydro-pyran-4-yloxy, tetrahydro-pyran-3-yloxy, cyclobutyloxy, oxepan-4-yloxy, oxepan-3-yloxy, cyclobutylmethoxy, cyclopropylmethoxy, tetrahydro-thiophen-3-yloxy, tetrahydro-thiopyran-4-yloxy, 1-methyl-pyrrolidin-3-yloxy, 1-acetyl-pyrrolidin-3-yloxyl, thiepan-3-yloxy, thiepan-4-yloxy, 1-methyl-piperidin-4-yloxy, 1-acetyl-piperidin-4-yloxy, 1-isopropyl-azepan-4-yloxy, 1-acetyl-azepan-4-yloxy, 1-ethyl-azepan-3-yloxy, or 1-acetyl-azepan-3-yloxy.

11. A compound as defined in claim 1, wherein —OCHR$^3$R$^4$ is tetrahydro-furan-3-yloxy, 3-methyl-oxetan-3-ylmethoxy, cyclopentyloxy, cyclohexyloxy, or tetrahydro-pyran-4-yloxy.

12. A compound as defined in claim 6, wherein —OCHR³R⁴ is tetrahydro-furan-3-yloxy, 3-methyl-oxetan-3-ylmethoxy, cyclopentyloxy, cyclohexyloxy, or tetrahydro-pyran-4-yloxy.

13. A compound as defined in claim 5, wherein —OCHR³R⁴ is tetrahydro-pyran-4-yloxy and m is 2.

14. A compound selected from the group consisting of:
(4-Isopropyl-piperazin-1-yl)-[6-(tetrahydro-furan-3-yloxy)-pyridin-3-yl]-methanone;
(4-Isopropyl-[1,4]diazepan-1-yl)-[6-(tetrahydro-furan-3-yloxy)-pyridin-3-yl]-methanone;
(4-Cyclopropyl-[1,4]diazepan-1-yl)-[6-(tetrahydro-furan-3-yloxy)-pyridin-3-yl]-methanone;
(4-Cyclobutyl-[1,4]diazepan-1-yl)-[6-(tetrahydro-furan-3-yloxy)-pyridin-3-yl]-methanone;
(4-Isopropyl-piperazin-1-yl)-[6-(3-methyl-oxetan-3-ylmethoxy)-pyridin-3-yl]-methanone;
(4-Isopropyl-[1,4]diazepan-1-yl)-[6-(3-methyl-oxetan-3-ylmethoxy)-pyridin-3-yl]-methanone;
(4-Cyclobutyl-[1,4]diazepan-1-yl)-(6-cyclopentyloxy-pyridin-3-yl)-methanone;
(4-Cyclobutyl-[1,4]diazepan-1-yl)-(6-cyclohexyloxy-pyridin-3-yl)-methanone;
(4-Cyclobutyl-[1,4]diazepan-1-yl)-[6-(tetrahydro-pyran-4-yloxy)-pyridin-3-yl]-methanone;
6-(4-Cyclopropyl-[1,4]diazepane-1-carbonyl)-3-(tetrahydro-furan-3-yloxy)-pyridine-2-carbonitrile;
3-Cyclopentyloxy-6-(4-cyclopropyl-[1,4]diazepane-1-carbonyl)-pyridine-2-carbonitrile;
3-Cyclohexyloxy-6-(4-cyclopropyl-[1,4]diazepane-1-carbonyl)-pyridine-2-carbonitrile;
(4-Isopropyl-[1,4]diazepan-1-yl)-[6-(tetrahydro-pyran-4-yloxy)-pyridin-3-yl]-methanone;
(4-Cyclopropyl-[1,4]diazepan-1-yl)-[6-(tetrahydro-pyran-4-yloxy)-pyridin-3-yl]-methanone;
(4-Cyclopentyl-[1,4]diazepan-1-yl)-[6-(tetrahydro-pyran-4-yloxy)-pyridin-3-yl]-methanone;
(4-Isopropyl-piperazin-1-yl)-[6-(tetrahydro-pyran-4-yloxy)-pyridin-3-yl]-methanone;
(4-Cyclopropyl-piperazin-1-yl)-[6-(tetrahydro-pyran-4-yloxy)-pyridin-3-yl]-methanone;
(4-Cyclobutyl-piperazin-1-yl)-[6-(tetrahydro-pyran-4-yloxy)-pyridin-3-yl]-methanone;
(4-Cyclopentyl-piperazin-1-yl)-[6-(tetrahydro-pyran-4-yloxy)-pyridin-3-yl]-methanone;
(4-Cyclobutyl-[1,4]diazepan-1-yl)-[5-(tetrahydro-pyran-4-yloxy)-pyridin-2-yl]-methanone;
(4-Cyclobutyl-[1,4]diazepan-1-yl)-[6-(tetrahydro-pyran-4-yloxy)-pyridin-2-yl]-methanone;
(6-Cyclobutoxy-pyridin-3-yl)-(4-cyclobutyl-[1,4]diazepan-1-yl)-methanone;
(4-Cyclobutyl-[1,4]diazepan-1-yl)-[6-(oxepan-4-yloxy)-pyridin-3-yl]-methanone;
(4-Cyclobutyl-[1,4]diazepan-1-yl)-[6-(oxepan-3-yloxy)-pyridin-3-yl]-methanone;
(4-Cyclobutyl-[1,4]diazepan-1-yl)-(6-cyclobutyl-methoxy-pyridin-3-yl)-methanone;
(4-Cyclobutyl-[1,4]diazepan-1-yl)-(6-cyclopropyl-methoxy-pyridin-3-yl)-methanone;
(4-Cyclobutyl-[1,4]diazepan-1-yl)-[6-(tetrahydro-thiophen-3-yloxy)-pyridin-3-yl]-methanone;
(4-Cyclobutyl-[1,4]diazepan-1-yl)-[6-(tetrahydro-thiopyran-4-yloxy)-pyridin-3-yl]-methanone;
(4-Cyclobutyl-[1,4]diazepan-1-yl)-[6-(1-methyl-pyrrolidin-3-yloxy)-pyridin-3-yl]-methanone;
1-{3-[5-(4-Cyclobutyl-[1,4]diazepane-1-carbonyl)-pyridin-2-yloxy]-pyrrolidin-1-yl}-ethanone;
(4-Cyclobutyl-[1,4]diazepan-1-yl)-[6-(thiepan-3-yloxy)-pyridin-3-yl]-methanone;
(4-Cyclobutyl-[1,4]diazepan-1-yl)-[6-(thiepan-4-yloxy)-pyridin-3-yl]-methanone;
(4-Cyclobutyl-[1,4]diazepan-1-yl)-[6-(1-methyl-piperidin-4-yloxy)-pyridin-3-yl]-methanone;
1-{4-[5-(4-Cyclobutyl-[1,4]diazepane-1-carbonyl)-pyridin-2-yloxy]-piperidin-1-yl}-ethanone;
(4-Cyclobutyl-[1,4]diazepan-1-yl)-[6-(1-isopropyl-azepan-4-yloxy)-pyridin-3-yl]-methanone;
1-{4-[5-(4-Cyclobutyl-[1,4]diazepane-1-carbonyl)-pyridin-2-yloxy]-azepan-1-yl}-ethanone;
(4-Cyclobutyl-[1,4]diazepan-1-yl)-[6-(1-ethyl-azepan-3-yloxy)-pyridin-3-yl]-methanone;
1-{3-[5-(4-Cyclobutyl-[1,4]diazepane-1-carbonyl)-pyridin-2-yloxy]-azepan-1-yl}-ethanone; and
(4-Cyclopropyl-piperazin-1-yl)-[6-(tetrahydro-pyran-3-yloxy)-pyridin-3-yl]-methanone;
or a pharmaceutically acceptable salt thereof.

15. A pharmaceutical composition, comprising:
(a) an effective amount of a compound of Formula (I):

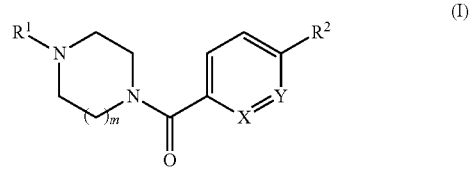

wherein
R¹ is —C₁₋₅alkyl or a saturated cycloalkyl group;
m is 1 or 2;
R² is —H or —OCHR³R⁴;
  where R³ is —H; and
  R⁴ is a cycloalkyl or heterocycloalkyl ring, unsubstituted or substituted with —C₁₋₄alkyl or acetyl;
  or, R³ and R⁴ taken together with the carbon to which they are attached form a cycloalkyl or heterocycloalkyl ring, unsubstituted or substituted with —C₁₋₄ alkyl or acetyl;
X is N or CH; and
Y is N or CRᵃ;
  where Rᵃ is —H, —OCHR³R⁴, —CH₂NRᵇRᶜ, —CN, —CO₂C₁₋₄alkyl, —CO₂H, or —CONRᵇRᶜ;
  Rᵇ and Rᶜ are each independently —H or —C₁₋₄alkyl;
with the proviso that one of X and Y is N and one of R² and Rᵃ is —OCHR³R⁴;
or a pharmaceutically acceptable salt thereof; and
(b) a pharmaceutically acceptable excipient.

16. A method of alleviating attention deficit hyperactivity disorder in a subject, comprising administering to the subject in need of such treatment an effective amount of a compound of Formula (I):

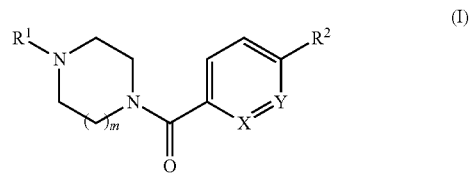

wherein
R¹ is —C₁₋₅alkyl or a saturated cycloalkyl group;
m is 1 or 2;

$R^2$ is —H or —OCHR$^3$R$^4$;
   where $R^3$ is —H; and
   $R^4$ is a cycloalkyl or heterocycloalkyl ring, unsubstituted or substituted with —C$_{1-4}$-alkyl or acetyl;
   or, $R^3$ and $R^4$ taken together with the carbon to which they are attached form a cycloalkyl or heterocycloalkyl ring, unsubstituted or substituted with —C$_{1-4}$-alkyl or acetyl;
X is N or CH; and
Y is N or CR$^a$;
   where R$^a$ is —H, —OCHR$^3$R$^4$, —CH$_2$NR$^b$R$^c$, —CN, —CO$_2$C$_{1-4}$alkyl, —CO$_2$H, or —CONR$^b$R$^c$;
   R$^b$ and R$^c$ are each independently —H or —C$_{1-4}$alkyl;
with the proviso that one of X and Y is N and one of R$^2$ and R$^a$ is —OCHR$^3$R$^4$;
or a pharmaceutically acceptable salt thereof.

\* \* \* \* \*